(12) United States Patent
Johnson

(10) Patent No.: US 10,871,379 B2
(45) Date of Patent: Dec. 22, 2020

(54) SYSTEMS AND METHODS OF DETERMINING LOCATIONS OF MEDICAL DEVICES RELATIVE TO WEARABLE DEVICES

(71) Applicant: ZOLL Medical Corporation, Chelmsford, MA (US)

(72) Inventor: Guy Robert Johnson, Gloucester, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 328 days.

(21) Appl. No.: 15/867,030

(22) Filed: Jan. 10, 2018

(65) Prior Publication Data

US 2018/0292226 A1    Oct. 11, 2018

Related U.S. Application Data

(63) Continuation of application No. 14/974,587, filed on Dec. 18, 2015, now Pat. No. 9,897,459.

(Continued)

(51) Int. Cl.
*E05B 47/06*  (2006.01)
*E05B 47/00*  (2006.01)
(Continued)

(52) U.S. Cl.
CPC .......... *G01C 21/362* (2013.01); *G01C 21/16* (2013.01); *G01C 21/20* (2013.01);
(Continued)

(58) Field of Classification Search
CPC .............. G01C 21/362; G01C 21/3632; G01C 21/3629; G01C 21/20; G01C 21/16;
(Continued)

(56) References Cited

U.S. PATENT DOCUMENTS 6,292,687 B1    9/2001   Lowell et al.
6,681,003 B2    1/2004   Linder et al.
(Continued)

FOREIGN PATENT DOCUMENTS

WO    WO-2013086244 A1    6/2013

OTHER PUBLICATIONS

International Search Report and Written Opinion issued by the U.S. Patent and Trademark Office in International Application PCT/US2015/066720, dated Feb. 23, 2016 (13 pages).

*Primary Examiner* — Brian P Sweeney
(74) *Attorney, Agent, or Firm* — Finch & Maloney PLLC

(57) ABSTRACT

According to some aspects, a wearable device is provided. The wearable device includes a memory, one or more antennas, one or more processors coupled with the memory and the one or more antennas, a location manager component executable by the one or more processors and configured to determine a location of the wearable device, and a direction manager component executable by the one or more processors. The direction manager component may be configured to receive, via the one or more antennas, information descriptive of a location of the medical device, determine a path between the location of the wearable device and the location of the medical device, and provide information descriptive of the path.

20 Claims, 12 Drawing Sheets

Related U.S. Application Data

(60) Provisional application No. 62/096,668, filed on Dec. 24, 2014.

(51) Int. Cl.

| | | |
|---|---|---|
| *E05B 17/04* | (2006.01) | |
| *E05B 17/22* | (2006.01) | |
| *G01C 21/36* | (2006.01) | |
| *G16H 40/63* | (2018.01) | |
| *G01C 21/16* | (2006.01) | |
| *G01C 21/20* | (2006.01) | |
| *G06F 19/00* | (2018.01) | |
| *H04W 4/021* | (2018.01) | |
| *H04W 4/02* | (2018.01) | |
| *G16H 40/67* | (2018.01) | |

(52) U.S. Cl.
CPC ..... *G01C 21/3629* (2013.01); *G01C 21/3632* (2013.01); *G06F 19/00* (2013.01); *G06F 19/3418* (2013.01); *G16H 40/63* (2018.01); *G16H 40/67* (2018.01); *H04W 4/021* (2013.01); *H04W 4/025* (2013.01); *G01C 21/206* (2013.01)

(58) Field of Classification Search
CPC ... G01C 21/206; G06F 19/00; G06F 19/3418; G16H 40/67; G16H 40/63; H04W 4/025; H04W 4/021
USPC ........................................................ 701/500
See application file for complete search history.

(56) References Cited

U.S. PATENT DOCUMENTS

| | | |
|---|---|---|
| 8,904,214 B2 | 12/2014 | Volpe et al. |
| 9,230,171 B2 | 1/2016 | Starner et al. |
| 9,897,459 B2 | 2/2018 | Johnson |
| 2007/0273504 A1 | 11/2007 | Tran |
| 2011/0060378 A1 | 3/2011 | Tuysserkani |
| 2011/0106624 A1 | 5/2011 | Bonner et al. |
| 2011/0117878 A1 | 5/2011 | Barash et al. |
| 2012/0123223 A1 | 5/2012 | Freeman et al. |
| 2012/0190386 A1 | 7/2012 | Anderson |
| 2013/0046648 A1 | 2/2013 | Calman et al. |
| 2014/0114677 A1 | 4/2014 | Holmes |
| 2014/0266718 A1 | 9/2014 | Bongberg et al. |
| 2014/0292534 A1 | 10/2014 | Stever et al. |
| 2014/0368601 A1* | 12/2014 | deCharms ............. H04W 4/021 348/14.02 |
| 2015/0025917 A1 | 1/2015 | Stempora |
| 2015/0170504 A1 | 6/2015 | Jooste |
| 2015/0230022 A1 | 8/2015 | Sakai et al. |
| 2015/0279173 A1 | 10/2015 | Hyde et al. |
| 2016/0093197 A1 | 3/2016 | See et al. |
| 2016/0132046 A1 | 5/2016 | Beoughter et al. |
| 2016/0187153 A1 | 6/2016 | Johnson |
| 2016/0210834 A1 | 7/2016 | Dayal |
| 2016/0278652 A1 | 9/2016 | Kaib et al. |
| 2016/0302697 A1 | 10/2016 | Johnson |

\* cited by examiner

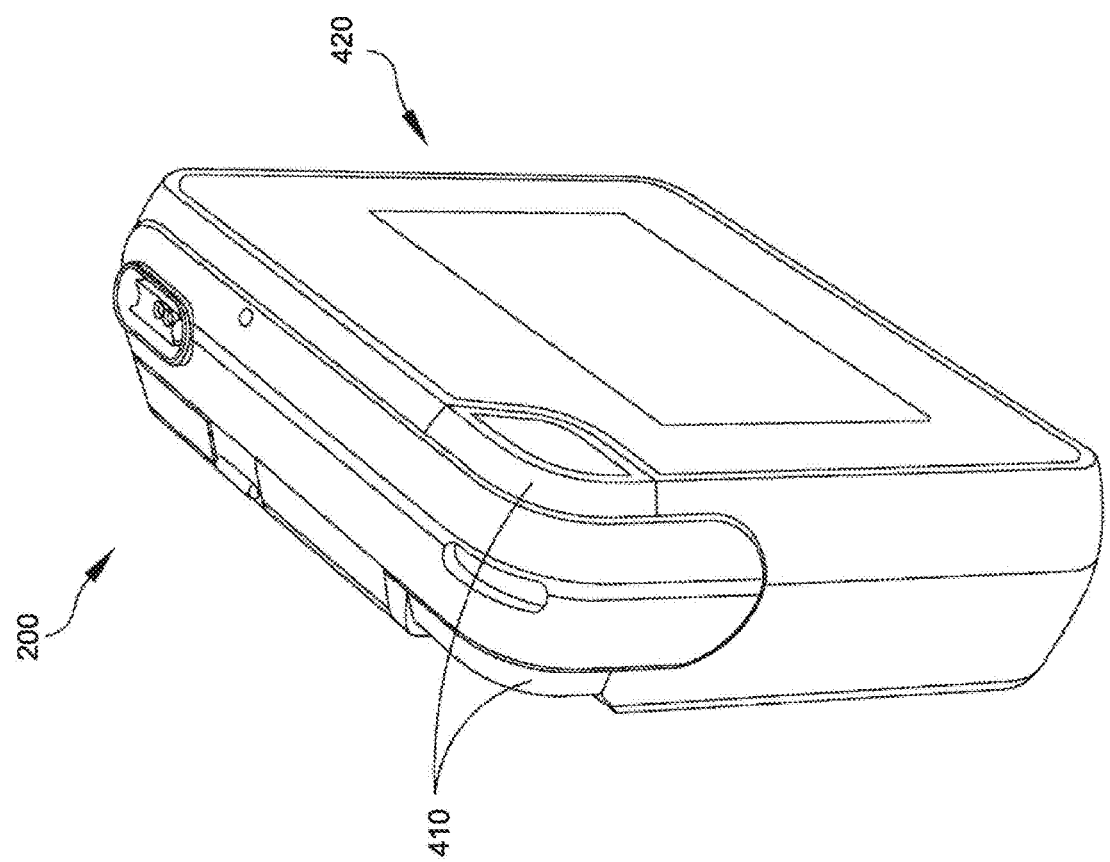
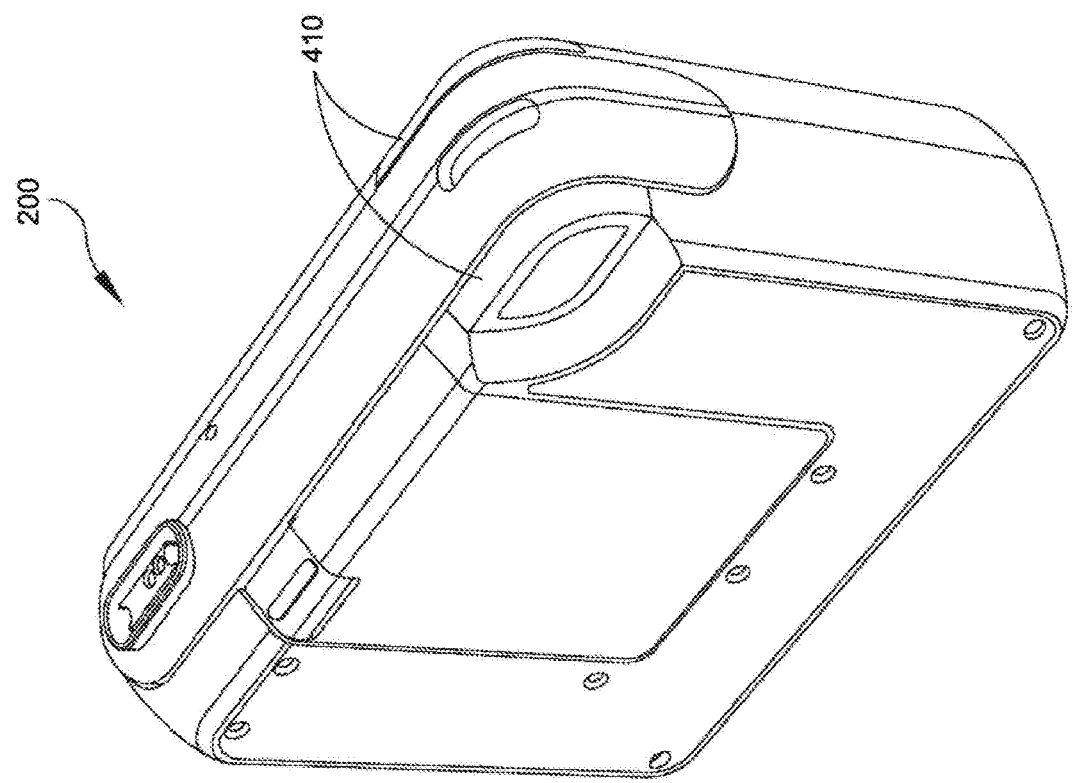

800

802 — First Level: Global Positioning System Information Sources

804 — Second Level: Cellular Information Sources

806 — Third Level: Wireless Local Area Network Access Point Information Sources

808 — Fourth Level: Other Medical Device Information Sources

810 — Fifth Level: Bluetooth Transmitter Information Sources

812 — Sixth Level: Radio-Frequency Identification Information Sources

814 — Seventh Level: Internal or Local Information Sources

FIG. 8

SYSTEMS AND METHODS OF DETERMINING LOCATIONS OF MEDICAL DEVICES RELATIVE TO WEARABLE DEVICES

RELATED APPLICATIONS

This application is a continuation of prior application Ser. No. 14/974,587, filed on Dec. 18, 2015, entitled "SYSTEMS AND METHODS OF DETERMINING LOCATIONS OF MEDICAL DEVICES RELATIVE TO WEARABLE DEVICES," which claims the benefit of U.S. Provisional Patent Application Ser. No. 62/096,668, filed on Dec. 24, 2014, entitled "SYSTEMS AND METHODS OF DETERMINING LOCATIONS OF MEDICAL DEVICES RELATIVE TO WEARABLE DEVICES," the contents of each of which are incorporated herein by reference in their entirety.

BACKGROUND

Technical Field

Aspects of the present invention relate to wearable devices, and more particularly to apparatus and processes of determining locations of medical devices relative to wearable devices.

Discussion

Medical devices monitor patients and/or administer therapy to patients. Some medical devices have a small physical footprint, are lightweight, and are therefore portable by patients, rescuers, or other medical personnel. These portable medical devices are prescribed in both in-patient and out-patient settings. Thus portable medical devices may be used in a wide variety of indoor and outdoor environments.

SUMMARY

Aspects and embodiments of the present invention provide for processes and apparatus for determining the location of medical devices and determining the location of medical devices relative to wearable devices. For instance, in accordance with one embodiment, a medical device is configured to accurately determine its location. In making this determination, the medical device executes a robust process that consistently and accurately determines the location of the medical device regardless of whether the device is located indoors, where global positioning system (GPS) signals are weak, or outdoors. For example, in some embodiments, the medical device is configured to scan for a plurality of location information sources. The medical device then combines the location information from all of the available location information sources to accurately determine the location of the medical device. By referencing a plurality of location information sources, the medical device increases the reliability of the location determination process because the system is not entirely dependent upon a single source of location information, such as a GPS signal reception. Also, in some embodiments, the medical device is configured to transmit the location of the medical device to a remote system operated by a medical dispatcher or other medical personnel in the area to assist the medical personnel in locating and providing medical care to the patient. For example, the medical personnel may wear one or more wearable devices that receive the location of the medical device, determine a path between the wearable device and the medical device, and provide instructions to the medical personnel to guide the medical personnel to locate the medical device.

According to one aspect, a medical device capable of determining its location is provided. The medical device comprises a memory, one or more antennas, one or more processors coupled with the memory and the one or more antennas, a location manager component executable by the one or more processors. The location manager component is configured to receive first location information from a first location information source and second location information from a second location information source, to rank the first location information source and the second location information source according to a hierarchy of location information sources, the hierarchy of location information sources specifying that the first location information source is of higher rank than the second location information source, determine an approximate location of the medical device based on the first location information, and improve, responsive to the receipt of the first location information and the second location information, the accuracy of the approximate location based on the second location information.

According to one embodiment, the location manager component is further configured to receive the first location information from at least one of a global positioning system, a wireless local area network access point, another medical device, a BLUETOOTH device, and a radio-frequency identification device. According to one embodiment, the location manager component is further configured to rank the global positioning system higher than other available location information sources.

According to one embodiment, the location manager component is further configured to transmit the approximate location of the medical device. According to one embodiment, the medical device is a first medical device and the location manager component is further configured to transmit the approximate location of the first medical device to a second medical device. According to one embodiment, the location manager component is further configured to transmit the approximate location of the first medical device to a remote system via the second medical device.

According to one embodiment, the location manager component is further configured to receive the first location information from a wireless local area network access point, and the location manager component is further configured further configured to determine the approximate location of the medical device by querying a database of wireless local area network access point locations to determine a location of the wireless local area network access point. According to one embodiment, the location manager component is further configured to determine the approximate location of the medical device by determining a distance between the medical device and the wireless local area network access point at least in part by measuring a signal strength received from the wireless local area network access point. According to one embodiment, the database of wireless local area network access point locations is stored in the memory of the medical device and location manager component is further configured to query the database stored in the memory of the medical device.

According to one embodiment, the medical device is a first medical device, the first location information source is a second medical device, and wherein the location manager component is further configured to determine the approximate location of the medical device by determining an approximate location of the second medical device.

According to one aspect, a method of determining location using a medical device, the medical device including one or more processors coupled with a memory and one or more antennas, is provided. The method comprises receiving first location information from a first location information source, receiving second location information from a second location information source, ranking the first location information source and the second location information source according to a hierarchy of location information sources, the hierarchy of location information sources specifying that the first location information source is of higher rank than the second location information source, determining an approximate location of the medical device based on the first location information, and improving, responsive to receiving the first location information and the second location information, the accuracy of the approximate location based on the second location information.

According to one embodiment, receiving the first location information from the first location information source includes receiving the first location information from at least one of a global positioning system, a wireless local area network access point, another medical device, a BLUETOOTH device, and a radio-frequency identification device. According to one embodiment, ranking the first location information source and the second location information source according to a hierarchy of location information sources includes ranking the global positioning system higher than other available location information sources.

According to one embodiment, the method further comprises transmitting the approximate location of the medical device. According to one embodiment, the medical device is a first medical device and transmitting the approximate location of the medical device includes transmitting the approximate location of the first medical device to a second medical device. According to one embodiment, the method further comprises transmitting the approximate location of the first medical device to a remote system via the second medical device.

According to one embodiment, receiving the first location information from the first location information source includes receiving the first location information from a wireless local area network access point and wherein determining the approximate location of the medical device includes querying a database of wireless local area network access point locations to determine a location of the wireless local area network access point. According to one embodiment, determining the approximate location of the medical device further includes determining a distance between the medical device and the wireless local area network access point at least in part by measuring a signal strength received from the wireless local area network access point. According to one embodiment, the database of wireless local area network access point locations is stored in the memory of the medical device and querying the database includes querying the database stored in the memory of the medical device.

According to one embodiment, the medical device is a first medical device, the first location information source is a second medical device, and wherein determining the approximate location of the medical device includes communicating with the second medical device to determine an approximate location of the second medical device.

According to one aspect, a non-transitory computer readable medium storing executable instructions configured to instruct at least one controller to perform a method of determining location using a medical device. The non-transitory computer readable medium storing executable instructions to instruct the at least one controller to rank the first location information source and the second location information source according to a hierarchy of location information sources, the hierarchy of location information sources specifying that the first location information source is of higher rank than the second location information source, to determine an approximate location of the medical device based on the first location information, and to improve, responsive to the receipt of the first location information and the second location information, the accuracy of the approximate location based on the second location information.

According to some aspects, a wearable device is provided. The wearable device includes a memory, one or more antennas, one or more processors coupled with the memory and the one or more antennas, a location manager component executable by the one or more processors and configured to determine a location of the wearable device, and a direction manager component executable by the one or more processors. The direction manager component may be configured to receive, via the one or more antennas, information descriptive of a location of the medical device, determine a path between the location of the wearable device and the location of the medical device, and provide information descriptive of the path.

In one embodiment, the wearable device comprises at least one of an earpiece, a pair of glasses, and a watch. In one embodiment, the wearable device further includes a speaker coupled to the one or more processors. In one embodiment, the direction manager component is further configured to provide the indication of the path to the subject at least in part by providing an audio message regarding the path via the speaker.

In one embodiment, the wearable device further comprises a display coupled to the one or more processors. In one embodiment, the wearable device comprises a pair of glasses and the display includes at least one display lens. In one embodiment, the direction manager component is further configured to provide the indication of the path at least in part by displaying directions regarding the path via the display.

In one embodiment, the direction manager component is further configured to determine whether the wearable device is within a threshold distance of the medical device. In one embodiment, the direction manager component is further configured to transmit, via the one or more antennas, a notification to the medical device responsive to the wearable device being within the threshold distance of the medical device. In one embodiment, the notification includes an instruction for the medical device to issue an audible sound.

According to one aspect, a method for determining a location of a medical device is provided. The method includes receiving, by one or more antennas coupled with one or more processors, information descriptive of a location of the medical device, determining, by the one or more processors, a path between the location of the wearable device and the location of the medical device, and providing information descriptive of the path.

In one embodiment, guiding the subject to the medical device by the wearable device includes guiding the subject to the medical device by at least one of an earpiece, a pair of glasses, and a watch. In one embodiment, providing the information descriptive of the path includes providing, by a speaker coupled with the one or more processors, an audio message regarding the path.

In one embodiment, providing the information descriptive of the path includes providing, by a display coupled with the one or more processors, the information descriptive of the path. In one embodiment, providing, by a display coupled with the one or more processors, the information descriptive of the path includes providing, by at least one display lens of a pair of glasses coupled with the one or more processors, the information descriptive of the path. In one embodiment, providing, by a display coupled with the one or more processors, the information descriptive of the path includes displaying, by the display, directions regarding the path.

In one embodiment, the method further comprises determining whether the wearable device is within a threshold distance of the medical device. In one embodiment, the method further comprises transmitting, by the one or more antennas, a notification to the medical device responsive to the wearable device being within the threshold distance of the medical device. In one embodiment, transmitting the notification includes transmitting an instruction for the medical device to issue an audible sound.

According to one aspect, a medical device is provided. The medical device includes a memory, one or more antennas, one or more processors coupled with the memory and the one or more antennas, and a location manager component executable by the one or more processors. The location manager component may be configured to receive first location information from a first location information source and second location information from a second location information source, rank the first location information source and the second location information source according to a hierarchy of location information sources, the hierarchy of location information sources specifying that the first location information source is of higher rank than the second location information source, determine an approximate location of the medical device based on the first location information, improve, responsive to the receipt of the first location information and the second location information, the accuracy of the approximate location based on the second location information, and transmit, via the one or more antennas, the approximate location to a wearable device.

In one embodiment, the wearable device includes a memory, one or more antennas, one or more processors coupled with the memory and the one or more antennas, a location manager component executable by the one or more processors and configured to determine a location of the wearable device, and a direction manager component executable by the one or more processors. The direction manager component may be configured to receive, via the one or more antennas, information descriptive of a location of the medical device, determine a path between the location of the wearable device and the location of the medical device, and provide information descriptive of the path.

Still other aspects, embodiments, and advantages of these exemplary aspects and embodiments, are discussed in detail below. Moreover, it is to be understood that both the foregoing information and the following detailed description are merely illustrative examples of various aspects, and are intended to provide an overview or framework for understanding the nature and character of the claimed subject matter. Any embodiment disclosed herein may be combined with any other embodiment. References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings:

FIGS. 4A-B are illustrations of one example of a medical device controller for an ambulatory medical device;

FIG. 8 is an illustration of one example hierarchy of location information sources;

DETAILED DESCRIPTION

Some embodiments disclosed herein generally relate to determining an indoor or outdoor location of a medical device and/or a wearable device. Location determination indoors is a challenging problem because of building infrastructure. Reinforced concrete, for example, highly attenuates and reflects electromagnetic waves, such as GPS signals emitted by satellites. Accordingly, in some embodiments, the device is capable of accessing a plurality of location information sources including, but not limited to, GPS information sources, Wireless Local Area Networks (WLAN) access point information sources, BLUETOOTH information sources, radio-frequency identification (RFID) sources, and location information available from other medical devices. Embodiments may use any combination of these location information sources to form an accurate determination of the location of the device. In addition, the location of the device may be transmitted to medical personnel. For example, the medical device may transmit the building address and floor where a patient is located to a medical dispatcher or a wearable device worn by medical personnel may transmit the location of the wearable device (and any associated subject) to a nearby ambulance.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Medical Device Location System

Figure 1:
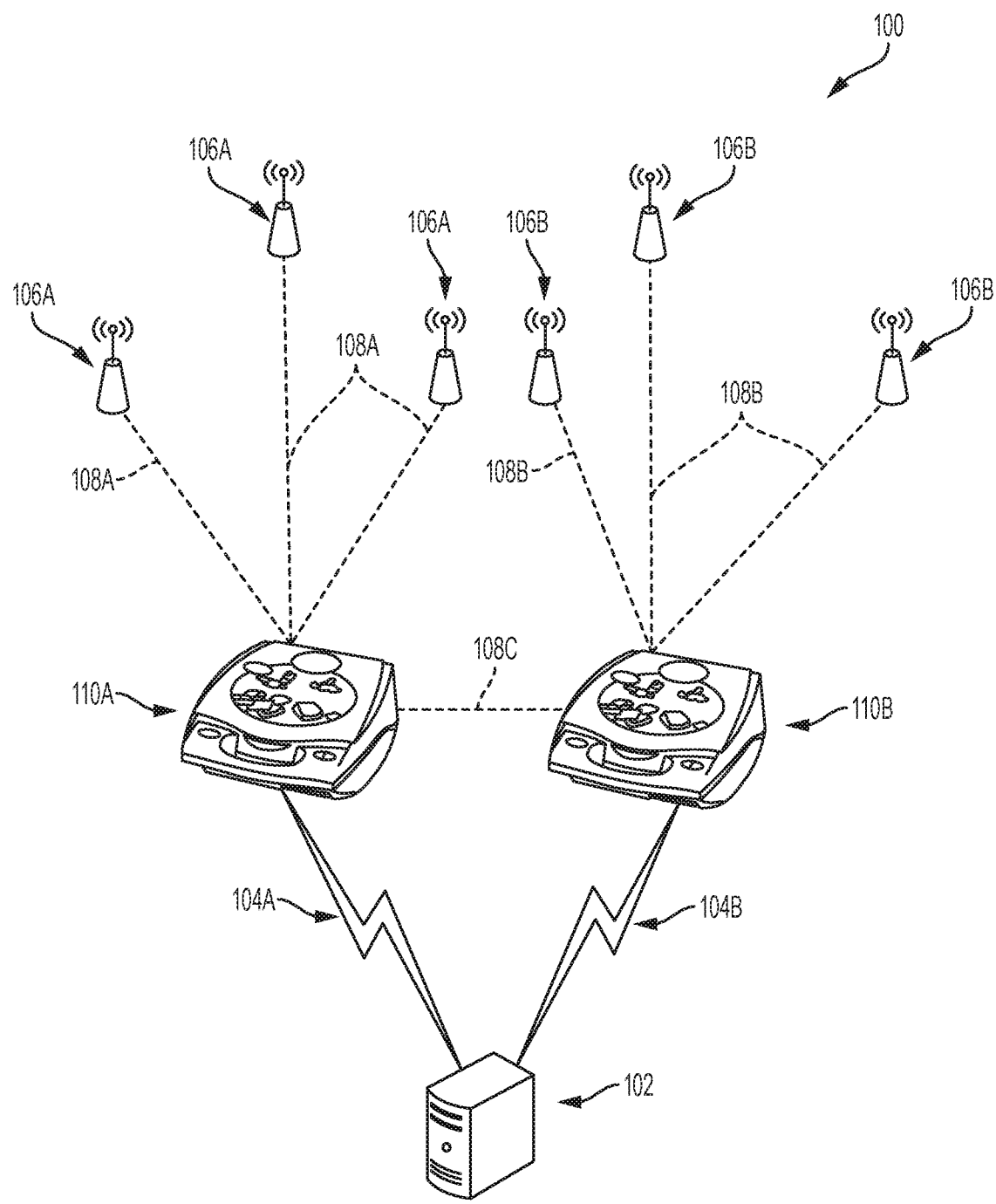
FIG. 1 is an illustration of one example of a medical device location system.

Various embodiments of the present invention include location systems that automatically determine locations of medical devices, such as the medical devices described herein. These location systems utilize a plurality of location information sources to determine locations of medical devices. One embodiment of a location system in accordance with the present invention is illustrated in FIG. 1. The medical device location system 100 includes a central server 102, medical devices 110A-B, communication links 104A-B, location information sources 106A-B, and location information links 108A-C. As depicted in FIG. 1, the medical device can include a plurality of automatic external defibrillator (AED) devices.

The medical devices 110A-B scan for location information sources 106 with signal strengths above a threshold. The location information sources 106 may include, but are not limited to, GPS information sources, WLAN access point information sources, location information sources available from other medical devices, BLUETOOTH information sources, and RFID information sources. The medical device 110A-B may include corresponding docking stations. Example docking stations for AEDs are disclosed in co-pending U.S. patent application Ser. No. 14/227,197, titled "SYSTEM AND METHOD FOR WIRELESS AED DOCKING," filed Mar. 27, 2014, which is hereby incorporated herein by reference in its entirety. The medical device docking stations may provide power to the medical device (e.g., through inductive power transfer) and/or communicate (e.g., through a Universal Serial Bus connection) with the medical device. Any combination of the processes described herein may be performed on the medical device or a corresponding medical device docking station.

In one embodiment, the medical device 110A detects GPS, WLAN access point, and BLUETOOTH location information sources represented by the three location information sources 106A and their corresponding location information links 108A. The GPS location information source may be one or more GPS satellites. The WLAN access point information source and the BLUETOOTH location information source may be any device equipped with these communication technologies that have a relatively fixed location. For example, medical device charging and/or docking stations may be equipped with WLAN or BLUETOOTH communication technology, and can serve as WLAN and/or BLUETOOTH location information sources (such charging and/or docking station can also be equipped with RFID communication technology and serve as a RFID location information source (not shown in FIG. 1)). The BLUETOOTH location information source may, in some embodiments, use BLUETOOTH LOW ENERGY (BLE) technology; such location information sources may also be referred to as BLE Beacons.

The received GPS signal may be used to compute, to a predefined precision and probability, initial location information for the medical device. For instance, the medical device may calculate a 50 meter radius circle within which the medical device has a 99% chance of being located.

The medical device 110A may then proceed to utilize additional location information sources 106A to increase the accuracy of the location information (e.g., to reduce the size of the 50 meter radius circle). In some embodiments, the medical device 110A is configured to increase the accuracy of the location information by determining whether the location information sources 106A with which it can communicate are associated with predefined locations.

In the example illustrated in FIG. 1, the medical device 110A queries a coordinate database in the central server 102 via the communication link 104A. The coordinate database stores coordinates of (or other location information associated with) WLAN access points, BLUETOOTH sources, and RFID tags. The central server 102 returns coordinates (or other relevant location information) associated with the BLUETOOTH source and the WLAN access point. Other relevant location information may include, but is not limited to, the signal power emitted by the source. The medical device then analyzes the signal strengths received from the WLAN access point and the BLUETOOTH source to determine the distance between the medical device and the sources. For example, the distance between the source location and the medical device may be calculated using a free-space path loss (FSPL) calculation that models signal power reduction in free-space over straight line distances. It is appreciated that the signal strength analysis may be performed by the central server 102 due to the power hungry nature of the calculation. Accordingly, in one embodiment, the medical device 110A transmits the received signal strength of the WLAN access point and BLUETOOTH source to the central server 102. The central server 102 then returns the calculated result (e.g., the location of the medical device) back to the medical device 110A or transmits the result directly to a remote system (e.g., a medical dispatching system). In addition, some or all of the calculations associated with determining the medical device location may be performed by the central server 102 to reduce the required processing capability and power consumption of the medical device. For example, in one embodiment, medical device 110A transmits all of the information associated with the available location information sources to the central server 102. The central server 102 then calculates the location of the medical device and returns simply the final computed location to the medical device. In some embodiments, the central server 102 may also transmit the final computed location to a computer system external to the medical device location system 100.

The information gathered from the WLAN access point and BLUETOOTH location information sources may then be used by the medical device 110A to estimate its location within the initial location information (e.g., 50 meter radius circle) computed based upon the GPS location information. It is appreciated that RFID location information sources may be analyzed in a fashion similar to that of BLUETOOTH and WLAN access point location information sources. The medical device 110A may include an RFID reader and may utilize the coordinate database in the central server 102 containing information regarding the location of the RFID tag or tags detected in the area. For example, where the medical device is an AED, the AED may detect an RFID tag in the docking station of the AED.

In other embodiments, some or all of the functionality of the central server 102 is performed locally by the medical devices. For example, the medical devices may include or have access to a local copy of the database of WLAN access points, BLUETOOTH sources, and RFID tags. The local copy of the database could also be a subset based upon knowledge of the general area where the medical device is deployed. For example, the medical device may be deployed in an ambulance that serves a specific metropolitan area. The medical device may have a local copy of the database of WLAN access points, BLUETOOTH sources, and RFID tags only in the specific metropolitan area.

The medical device 110A of FIG. 1 also has a location information connection 108C to another medical device 110B. The location information connection 108C between the medical devices 110A-B allows medical device 110A to access information sources within the range of medical device 110B and vice versa. It is appreciated that any of the location information links 108A-C may carry data in addition to location information. For example, the medical device 110A may lose its connection 104A to the central server 102. The medical device 110A may route the data through medical device 110B via location information link 108C and utilize the connection 104B between medical device 110B and the central server 102.

It is appreciated that more than two medical devices 110A-B may be interconnected as shown in FIG. 1. Any number of medical devices may be interconnected to form a rudimentary Ad Hoc network. The Ad Hoc network enables any medical device to communicate with any other medical device in the network in addition to gaining the location information and communication links of any other medical device in the network. In one embodiment, one medical device among a plurality of devices in the Ad Hoc network has an internet connection. In this embodiment, all of the medical devices in the Ad Hoc network have internet connectivity because data may be routed through the one medical device with the internet connection. In addition, the medical devices may have access to any locally stored information on any other medical device in the Ad Hoc network. For example, one medical device may have a local copy of the database of WLAN access points, BLUETOOTH sources, and RFID tags. The other medical devices in the Ad Hoc network may access the copy of the database of WLAN access points, BLUETOOTH sources, and RFID tags on the one medical device rather than accessing the central server 102.

The medical devices 110A-B may also utilize location information from mobile devices (e.g., cellular phones and tablets). For example, individuals within range of the medical device may have an application on their mobile device that enables the medical device to communicate with the mobile device (e.g., via BLUETOOTH) and query the phone for location information. The location information provided by the phone may be based on GPS, cellular triangulation or WLAN access point data, or any combination thereof. In addition, the medical devices may route data to the central server 102 via the internet connection of the mobile device. The locating determination system described with regard to FIG. 1 may be performed by a medical device controller integrated with or communicatively coupled with the medical device.

Medical Device Controller

Figure 2:
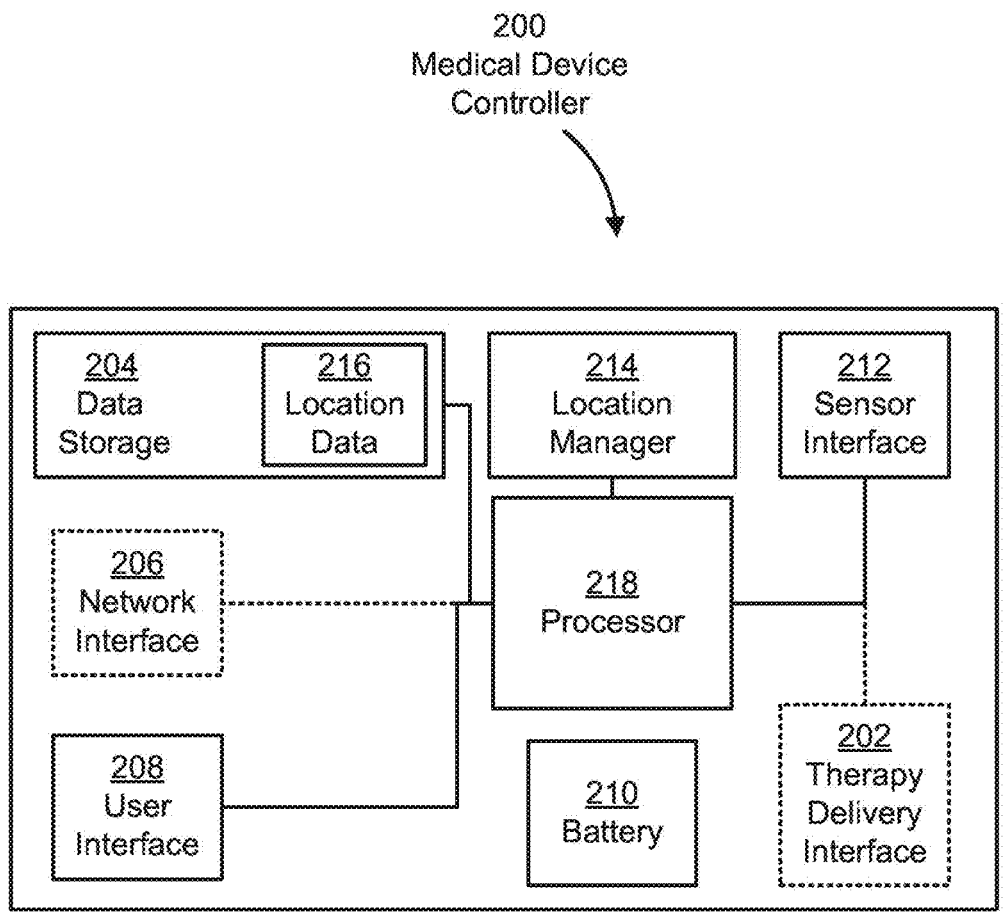
FIG. 2 is a functional schematic of one example of a medical device controller.

FIG. 2 illustrates a medical device controller 200 that is configured to monitor a patient and the patient's environment for events of interest and to determine the location of the medical device. The medical device controller 200 may, for example, be configured for use in a wearable defibrillator or an Automated External Defibrillator (AED). As shown in FIG. 2, the medical device controller 200 includes a processor 218, a sensor interface 212, a location manager 214, a therapy delivery interface 202, data storage 204, a communication network interface 206, a user interface 208, and a battery 210. The data storage 204 includes location data 216. Further, in this illustrated example, the battery 210 is a rechargeable 3 cell 2200 mAh lithium ion battery pack that provides electrical power to the other device components with a minimum 24 hour runtime between charges. It is appreciated that the battery capacity, runtime, and type (e.g., lithium ion, nickel-cadmium, or nickel-metal hydride) may be changed to best fit the specific application of the medical device controller 200.

According to the embodiment illustrated in FIG. 2, the processor 218 is coupled to the sensor interface 212, the therapy delivery interface 202, the data storage 204, the network interface 206, and the user interface 208. The processor 218 performs a series of instructions that result in manipulated data which are stored in and retrieved from the data storage 204. According to a variety of embodiments, the processor 218 is a commercially available processor such as a processor manufactured by Texas Instruments, Intel, AMD, Sun, IBM, Motorola, Freescale, and ARM Holdings. However, the processor 218 may be any type of processor, multiprocessor or controller, whether commercially available or specially manufactured. For instance, according to one embodiment, the processor 218 may include a power conserving processor arrangement such as described in co-pending U.S. patent application Ser. No. 12/833,096, titled "SYSTEM AND METHOD FOR CONSERVING POWER IN A MEDICAL DEVICE," filed Jul. 9, 2010 (hereinafter the "'096 application"), which is hereby incorporated herein by reference herein in its entirety and attached as Appendix B. In another embodiment, the processor 218 is an Intel® PXA270.

In addition, in several embodiments the processor 218 is configured to execute a conventional real-time operating system (RTOS), such as RTLinux. In these embodiments, the RTOS may provide platform services to application software, such as some embodiments of the location manager 214 which is discussed further below. These platform services may include inter-process and network communication, file system management and standard database manipulation. One or more of many operating systems may be used, and embodiments are not limited to any particular operating system or operating system characteristic. For instance, in some embodiments, the processor 218 may be configured to execute a non-real time operating system, such as BSD or GNU/Linux.

In some embodiments, the location manager 214 is configured to determine the location of the medical device. Particular examples of the processes performed by the location manager 214 are discussed further below with reference to FIGS. 6-7 and within the Location Determination Processes section.

The location manager 214 may be implemented using hardware or a combination of hardware and software. For instance, in one embodiment, the location manager 214 is implemented as a software component that is stored within the data storage 212 and executed by the processor 218. In this embodiment, the instructions included in the location manager 214 program the processor 218 to determine the location of the medical device. In other embodiments, location manager 214 may be an application-specific integrated circuit (ASIC) that is coupled to the processor 218 and tailored to determine the location of the medical device. Thus, embodiments of the location manager 214 are not limited to a particular hardware or software implementation.

In some embodiments, the components disclosed herein, such as the location manager 214, may read parameters that affect the functions performed by the components. These parameters may be physically stored in any form of suitable memory including volatile memory, such as RAM, or non-volatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some embodiments provide for both system and user interfaces, as may be implemented using the user interface 208, that allow external entities to modify the parameters and thereby configure the behavior of the components.

The data storage 204 includes a computer readable and writeable nonvolatile data storage medium configured to store non-transitory instructions and data. In addition, the data storage 204 includes processor memory that stores data during operation of the processor 218. In some embodiments, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several embodiments, the processor 218 causes data to be read from the nonvolatile data storage medium into the processor memory prior to processing the data. In these embodiments, the processor 218 copies the data from the processor memory to the non-volatile storage medium after processing is complete. A variety of components may manage data movement between the non-volatile storage medium and the processor memory and embodiments are not limited to particular data management components. Further, embodiments are not limited to a particular memory, memory system or data storage system.

The instructions stored on the data storage 204 may include executable programs or other code that can be executed by the processor 218. The instructions may be persistently stored as encoded signals, and the instructions may cause the processor 218 to perform the functions described herein. The data storage 204 also may include information that is recorded, on or in, the medium, and this information may be processed by the processor 218 during execution of instructions. The medium may, for example, be optical disk, magnetic disk or flash memory, among others, and may be permanently affixed to, or removable from, the medical device controller 200.

In some embodiments, the location data 216 includes data used by the location manager 214 to determine the location of the medical device. More particularly, according to the illustrated embodiment, the location data 216 includes information that identifies the plurality of location information sources and any information associated with the plurality of location information sources. For example, the location data may include the GPS coordinates associated with a specific location information source (e.g., an RFID tag, a BLUETOOTH source, or a WLAN access point).

As illustrated in FIG. 2, the location manager 214 and the location data 216 are separate components. However, in other embodiments, the location manager 214 and the location data 216 may be combined into a single component or re-organized so that a portion of the data included in the location manager 214, such as executable code that causes the processor 218 to determine the location of the medical device, resides in the location data 216, or vice versa. Such variations in these and the other components illustrated in FIG. 2 are intended to be within the scope of the embodiments disclosed herein.

The location data 216 may be stored in any logical construction capable of storing information on a computer readable medium including, among other structures, flat files, indexed files, hierarchical databases, relational databases or object oriented databases. These data structures may be specifically configured to conserve storage space or increase data exchange performance. In addition, various embodiments organize the location data 216 into particularized and, in some cases, unique structures to perform the functions disclosed herein. In these embodiments, the data structures are sized and arranged to store values for particular types of data, such as integers, floating point numbers, character strings, arrays, linked lists, and the like.

As shown in FIG. 2, the medical device controller 200 includes several system interface components 202, 206, and 212. Each of these system interface components is configured to exchange, i.e. send or receive, data with one or more specialized devices that may be located within the housing of the medical device controller 200 or elsewhere. The components used by the interfaces 202, 206, and 212 may include hardware components, software components or a combination of both. Within each interface, these components physically and logically couple the medical device controller 200 to the specialized devices. This physical and logical coupling enables the medical device controller 200 to communicate with and, in some instances, power or control the operation of the specialized devices. These specialized devices may include physiological sensors, therapy delivery devices, and computer networking devices.

According to various embodiments, the hardware and software components of the interfaces 202, 206 and 212 implement a variety of coupling and communication techniques. In some embodiments, the interfaces 202, 206, and 212 use leads, cables or other wired connectors as conduits to exchange data between the medical device controller 200 and specialized devices. In other embodiments, the interfaces 202, 206, and 212 communicate with specialized devices using wireless technologies such as radio frequency or infrared technology. The software components included in the interfaces 202, 206, and 212 enable the processor 218 to communicate with specialized devices. These software components may include elements such as objects, executable code, and populated data structures. Together, these software components provide software interfaces through which the processor 218 can exchange information with specialized devices. Moreover, in at least some embodiments where one or more specialized devices communicate using analog signals, the interfaces 202, 206, and 212 further include components configured to convert analog information into digital information, and vice versa, to enable the processor 218 to communicate with specialized devices.

As discussed above, the system interface components 202, 206, and 212 shown in the embodiment of FIG. 2 support different types of specialized devices. For instance, the components of the sensor interface 212 couple the processor 218 to one or more physiological sensors such as a body temperature sensors, respiration monitors, and electrocardiogram (ECG) sensing electrodes, one or more environmental sensors such as atmospheric thermometers, airflow sensors, video sensors, audio sensors, accelerometers, GPS locators, and hygrometers. In these embodiments, the sensors may include sensors with a relatively low sampling rate, such as wireless sensors.

The components of the therapy delivery interface 202 couple one or more therapy delivery devices, such as capacitors, defibrillator electrodes, pacing electrodes, or mechanical chest compression devices, to the processor 218. It is appreciated that the functionality of the therapy delivery interface 202 may be incorporated into the sensor interface 212 to form a single interface coupled to the processor 218. In addition, the components of the network interface 206 couple the processor 218 to a computer network via a networking device, such as a bridge, router or hub. According to a variety of embodiments, the network interface 206 supports a variety of standards and protocols, examples of which include USB (via, for example, a dongle to a computer), TCP/IP, Ethernet, Wireless Ethernet, BLUETOOTH, ZigBee, M-Bus, CAN-bus, IP, IPV6, UDP, DTN, HTTP, FTP, SNMP, CDMA, NMEA and GSM. It is appreciated that the network interface 206 of medical device controller 200 may enable communication between other medical device controllers and/or wearable devices within a certain range.

To ensure data transfer is secure, in some embodiments, the medical device controller 200 can transmit data via the network interface 206 using a variety of security measures including, for example, TLS, SSL or VPN. In other embodiments, the network interface 206 includes both a physical interface configured for wireless communication and a physical interface configured for wired communication. According to various embodiments, the network interface 206 enables communication between the medical device controller 200 and a variety of personal electronic devices including, for example, computer enabled glasses, watches, and earpieces.

In one embodiment, the network interface 206 is also capable of transmitting and/or receiving information to assist in medical device location determination. This may be accomplished through one or more antennas integrated with or coupled to the network interface 206, and consequently coupled to the processor 218. For example, the one or more antennas may receive GPS signals from satellites. The GPS signals may be used to determine the location of the medical device with a given level of accuracy and/or used to determine the current time. In other embodiments, an RFID reader is integrated or coupled to the network interface 206, and subsequently coupled to the processor 218. The RFID reader may be used at least in part to determine the location of the medical device. For example, the medical device may have access to a coordinate database that includes RFID tag locations and determine its location at least in part by detecting an RFID tag with a known location within a given range of the medical device. The database may be stored locally in the memory of the medical device controller or in a central server. It is appreciated that the systems described above with regard to connecting to various networks (e.g., wireless Ethernet or BLUETOOTH) may be used as probes to find known reference points within a given range. For example, the medical device controller 200 may detect a WLAN access point or a BLUETOOTH source with known positions stored in a database accessible by the medical device controller 200. The medical device controller 200 may be able to determine its location at least in part by determining the distance between the medical device controller and the known location of the WLAN access point or BLUETOOTH source. This may be accomplished at least in part by analyzing the signal strength of the WLAN access point and BLUETOOTH source.

It is appreciated that the medical device location computation may be performed in a collaborative fashion with the central server to minimize the computations performed by the medical device controller. For example, the medical device may transmit the detected sources and their respective signal strengths. The central server may then compute the location of the medical device by analyzing the signal strengths and coordinates associated with the sources. The computed medical device location may then transmit to the medical device or a remote system (e.g., a remote system operated by medical personnel).

In another embodiment, the medical device controller combines a plurality of information sources to determine the location of the medical device with the highest level of accuracy possible. The medical device location computation may be performed consistent with a hierarchy of location information sources. For example, the highest ranked available location information source may be used to determine the medical device location with a given level of accuracy. Additional location information sources are then used to improve the level of accuracy of the medical device location.

Thus, the various system interfaces incorporated in the medical device controller 200 allow the device to interoperate with a wide variety of devices in various contexts. For instance, some embodiments of the medical device controller 200 are configured to perform a process of sending critical events and data to a centralized server via the network interface 206. An illustration of a process in accord with these embodiments is disclosed in U.S. Pat. No. 6,681, 003, titled "DATA COLLECTION AND SYSTEM MANAGEMENT FOR PATIENT-WORN MEDICAL DEVICES," issued on Jan. 20, 2004, which is hereby incorporated by reference herein in its entirety.

As illustrated in FIG. 2, the therapy delivery interface 202 and the network interface 206 are optional and may not be included in every embodiment. For instance, a heart rate monitor may employ the medical device controller 200 to issue alarms but may not include a therapy delivery interface 202 to treat cardiac abnormalities. Similarly, an ambulatory defibrillator may include the medical device controller 200 to provide alarm functionality but may not include a network interface 206 where, for example, the ambulatory defibrillator is designed to rely on the user interface 208 to announce alarms.

The user interface 208 shown in FIG. 2 includes a combination of hardware and software components that allow the medical device controller 200 to communicate with an external entity, such as a patient or other user. These components may be configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens, and speakers. In some embodiments, the electrodes include an illuminating element, such as an LED. In other embodiments, the printing devices include printers capable of rendering visual or tactile (Braille) output.

The medical device controller 200 has a variety of potential applications and is well suited to devices that notify external entities of a variety of events, some of which may require a predetermined response from the external entity. Predetermined responses may include any response that is appropriate given the event being reported. Predetermined responses may include acknowledgment of the alarm, entry of information indicating that the alarm is being addressed and rectification of the event or condition that triggered the alarm. Examples of devices to which the medical device controller 200 is well suited include critical care medical devices, such as a wearable ambulatory external defibrillator, an AED, or a mechanical chest compression device, such as the Autopulse® system from ZOLL Medical Corporation of Chelmsford, Mass.

Example Ambulatory Medical Device

Figure 3:
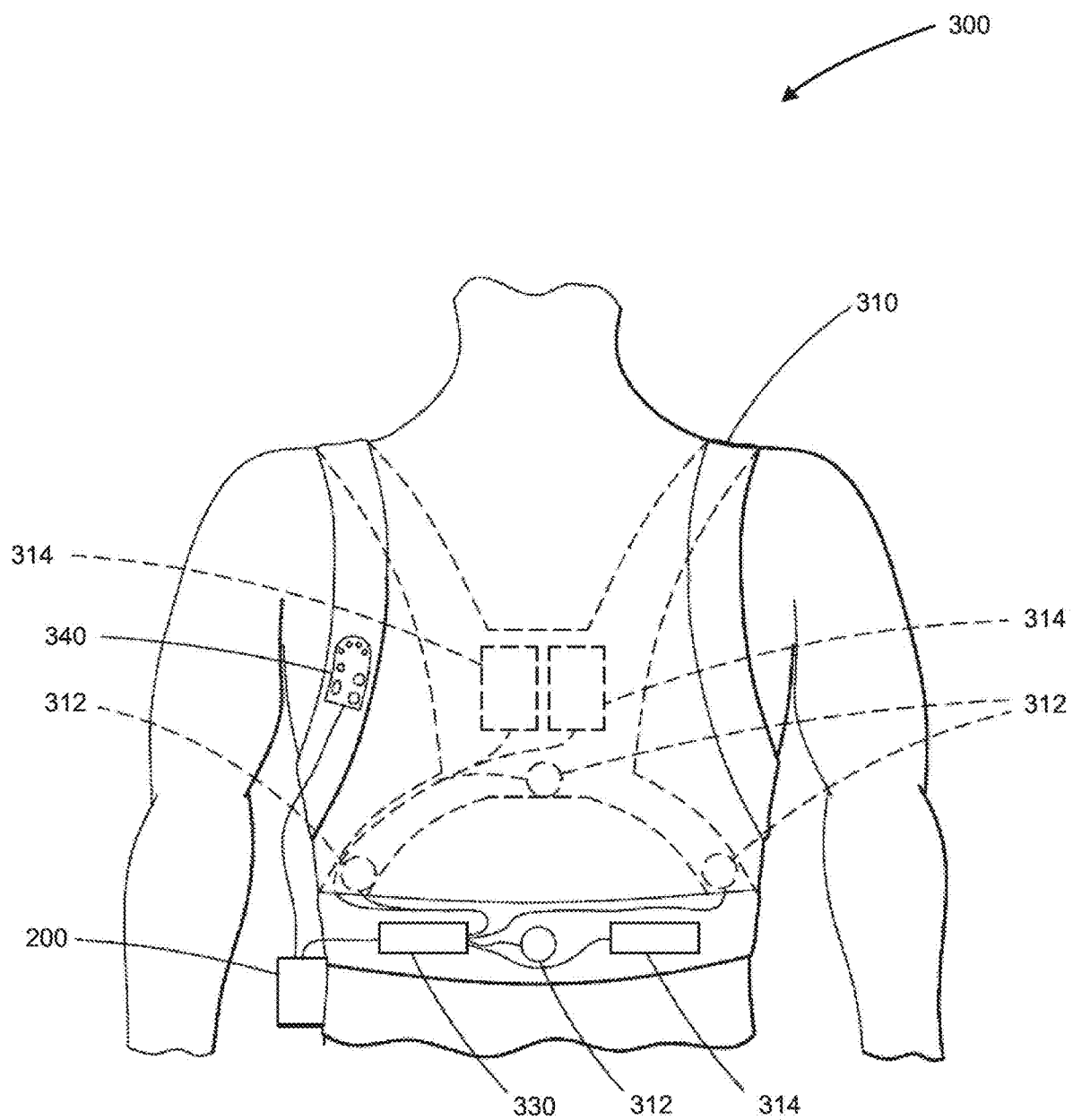
FIG. 3 is an illustration of one example of an ambulatory medical device.

In one embodiment, the medical device is a wearable defibrillator that includes a garment (e.g., a vest or belt) that is worn by the patient. The wearable defibrillator monitors the patient's ECG with sensing electrodes, detects life-threatening arrhythmias, and delivers a cardioverting or defibrillating shock through the therapy pads if treatment is necessary. FIG. 3 illustrates a wearable defibrillator, such as a LifeVest® wearable cardioverter defibrillator available from ZOLL Medical Corporation of Chelmsford, Mass. As shown, the wearable defibrillator 300 includes a harness 310 having a pair of shoulder straps and a belt that is worn about the torso of a patient. The wearable defibrillator 300 includes a plurality of ECG sensing electrodes 312 that are attached to the harness 310 at various positions about the patient's body and electrically coupled to the sensor interface 212 of the medical device controller 200 via a connection pod 330. The plurality of ECG sensing electrodes 312, which may be dry-sensing capacitance electrodes, are coupled to the medical device controller 200 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 312 may be disposed at varying locations about the patient's body.

The wearable defibrillator 300 also includes a plurality of therapy electrodes 314 that are electrically coupled to the medical device controller 200 via the connection pod 330 and which are configured to deliver one or more therapeutic defibrillating shocks to the body of the patient, if it is determined that such treatment is warranted. The connection pod 330 electrically couples the plurality of ECG sensing electrodes 312 and the plurality of therapy electrodes 314 to the therapy delivery interface 202 of the medical device controller 200, and may include electronic circuitry. The connection pod 330 may also include other electronic circuitry, such as a motion sensor or accelerometer through which patient activity may be monitored.

As shown in FIG. 3, the wearable defibrillator 300 also includes a user interface pod 340 that is electrically coupled to, or integrated in with, the user interface 208 of the medical device controller 200. The user interface pod 340 can be attached to the patient's clothing or to the harness 310, for example, via a clip (not shown) that is attached to a portion of the interface pod 340. Alternatively, the user interface pod 340 may simply be held in a person's hand. In some embodiments, the user interface pod 340 may communicate wirelessly with the user interface 208 of the medical device controller 200, for example, using a BLUETOOTH, Wireless USB, ZigBee, Wireless Ethernet, GSM, or other type of communication interface.

The user interface pod 340 includes a number of buttons by which the patient, or a bystander can communicate with the medical device controller 200, and a speaker by which the medical device controller 200 may communicate with the patient or the bystander. For example, where the medical device controller 200 determines that the patient is experiencing cardiac arrhythmia, the medical device controller 200 may issue an audible alarm via a speaker on the medical device controller 200 or the user interface pod 340 alerting the patient and any bystanders to the patient's medical condition. The medical device controller 200 may also instruct the patient to press and hold one or more buttons on the user interface 208 of the medical device controller 200 or on the user interface pod 340 to indicate that the patient is conscious, thereby instructing the medical device controller 200 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

In another embodiment, the functionality of the user interface pod 340 is integrated into the housing of the ambulatory medical device controller 200. FIGS. 4A-B illustrates such an example of the ambulatory medical device controller 200. The ambulatory medical device controller 200 includes two response buttons 410 on opposing sides of the housing of the ambulatory medical device controller 200. As shown in FIGS. 4A-B, the response buttons 410 are recessed to reduce the likelihood of accidental activation (e.g., a patient falling on the response button). The ambulatory medical device controller 200 also includes, in this embodiment, a display screen 420 and a speaker to enable the communication of audible and visual stimuli to the patient. It is appreciated that the response buttons 410 do not have to be placed on opposing sides of the housing as illustrated in FIGS. 4A-B. The response buttons, for example, may be located adjacent to each other in the housing the ambulatory medical device controller. The adjacent placement of the response buttons may make it easier for individuals with smaller hands or less dexterity to engage the response buttons.

Another example of a medical device is the ambulatory external defibrillator described in FIG. 3 of the '096 application. In at least one embodiment, the ambulatory defibrillator 300 illustrated in FIG. 3 of the '096 application may employ the medical device controller 200, as disclosed in the present application, as a substitute for the portable treatment controller 200 described in the '096 application. In such an embodiment, the ECG Electrodes and Therapy Pads illustrated in FIG. 3 of the '096 application may be logically and physically coupled to the medical device controller 200 via the sensor interface 212 and the therapy delivery interface 202, respectively. While some of the embodiments disclosed herein are directed to medical device controllers in wearable ambulatory medical devices, the medical device controller 200 is well suited for other medical devices including other types of AEDs.

Example Automated Medical Device

Figure 5:
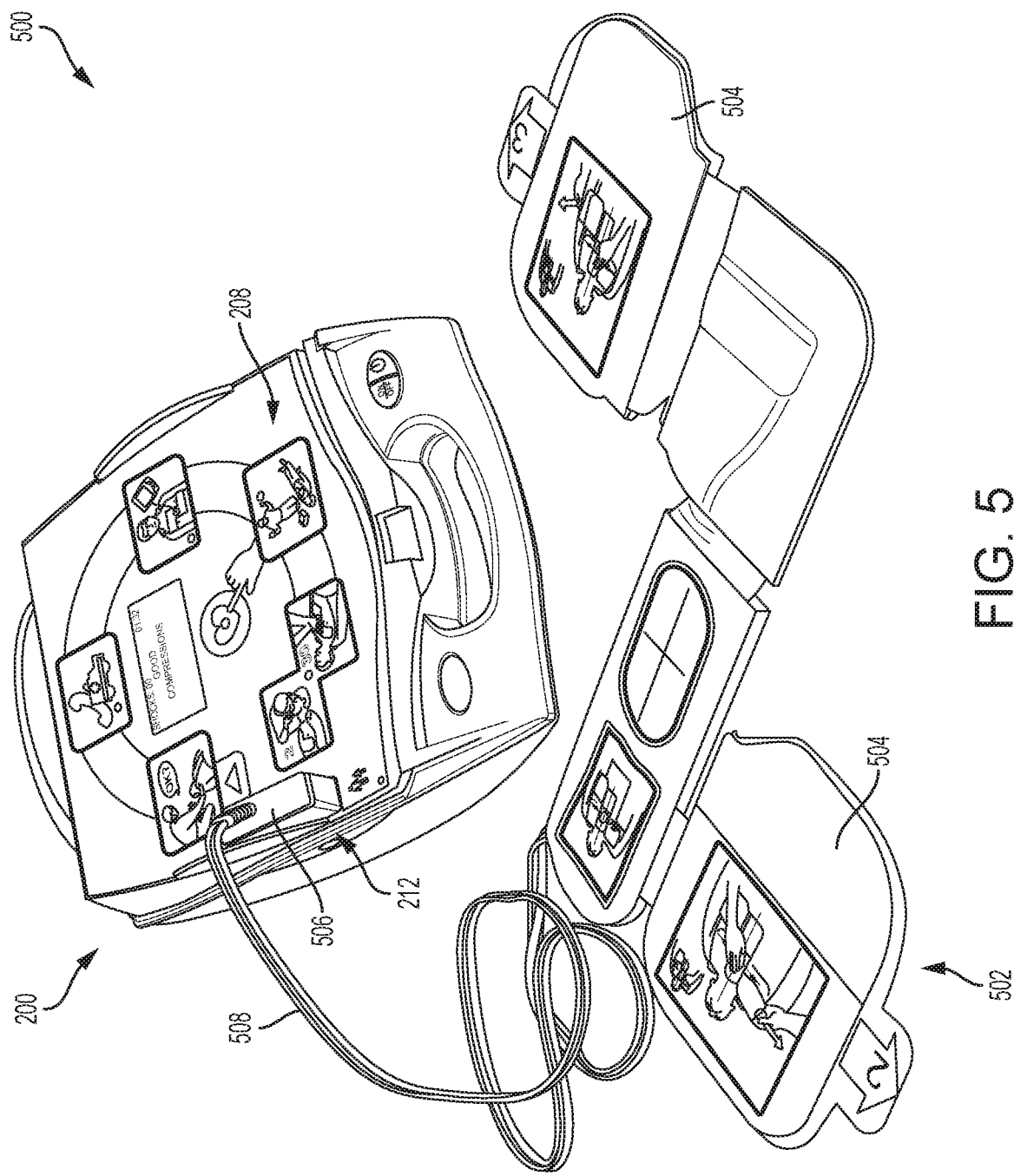
FIG. 5 is an illustration of one example of an external medical device.

In one embodiment, the medical device is an AED. AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED, in addition, may be configured to provide counseling to an operator as to how to perform cardiopulmonary resuscitation (CPR). FIG. 5 illustrates an AED, such as an automated external defibrillator available from ZOLL Medical Corporation of Chelmsford, Mass. As shown, the AED 500 includes a medical device controller 200 and an electrode assembly 502.

The electrode assembly 502 includes one or more sensing electrodes 504 (e.g., ECG sensors), one or more therapy electrodes 504 (e.g., defibrillation pads), a connector 506, wiring 508 electrically coupling the connector 506 to the one or more sensing electrodes 504 and one or more therapy electrodes 504. As shown in FIG. 5, the connector is configured to couple the electrode assembly 502 to the medical device controller 200 and, more specifically, the one or more sensing electrodes to the sensor interface 212 and the one or more therapy electrodes to the therapy delivery interface 202.

The medical device controller 200 of the AED 500 is configured to detect the cardiac rhythm of the patient and provide defibrillating shocks to the patient as appropriate. This process is similar to the process described with regard to medical device controller 200 of the ambulatory medical device 300. The user interface 208 of the AED 500 may include a variety of components configured to communicate with the operator including, but not limited to, a display screen, a speaker, and one or more buttons. In this embodiment, the AED 500 includes a display screen to display notifications to an operator. The notifications may provide instructions to the operator regarding the proper administration of CPR to the patient. The notifications on the display may be accompanied by audible alerts from the speaker to further assist the operator in administering CPR to the patient.

According to various embodiments, the AED 500 and the wearable defibrillator 300 utilize the network interface 206 of the medical device controller 200 to determine location information and transmit the location information to the appropriate medical personnel. While some of the embodiments disclosed herein are directed to medical devices for cardiac monitoring and treatment, other embodiments are directed to other types of medical devices that compute their location through a variety of processes executed by the medical device controller 200.

Location Determination Processes

Figure 6:
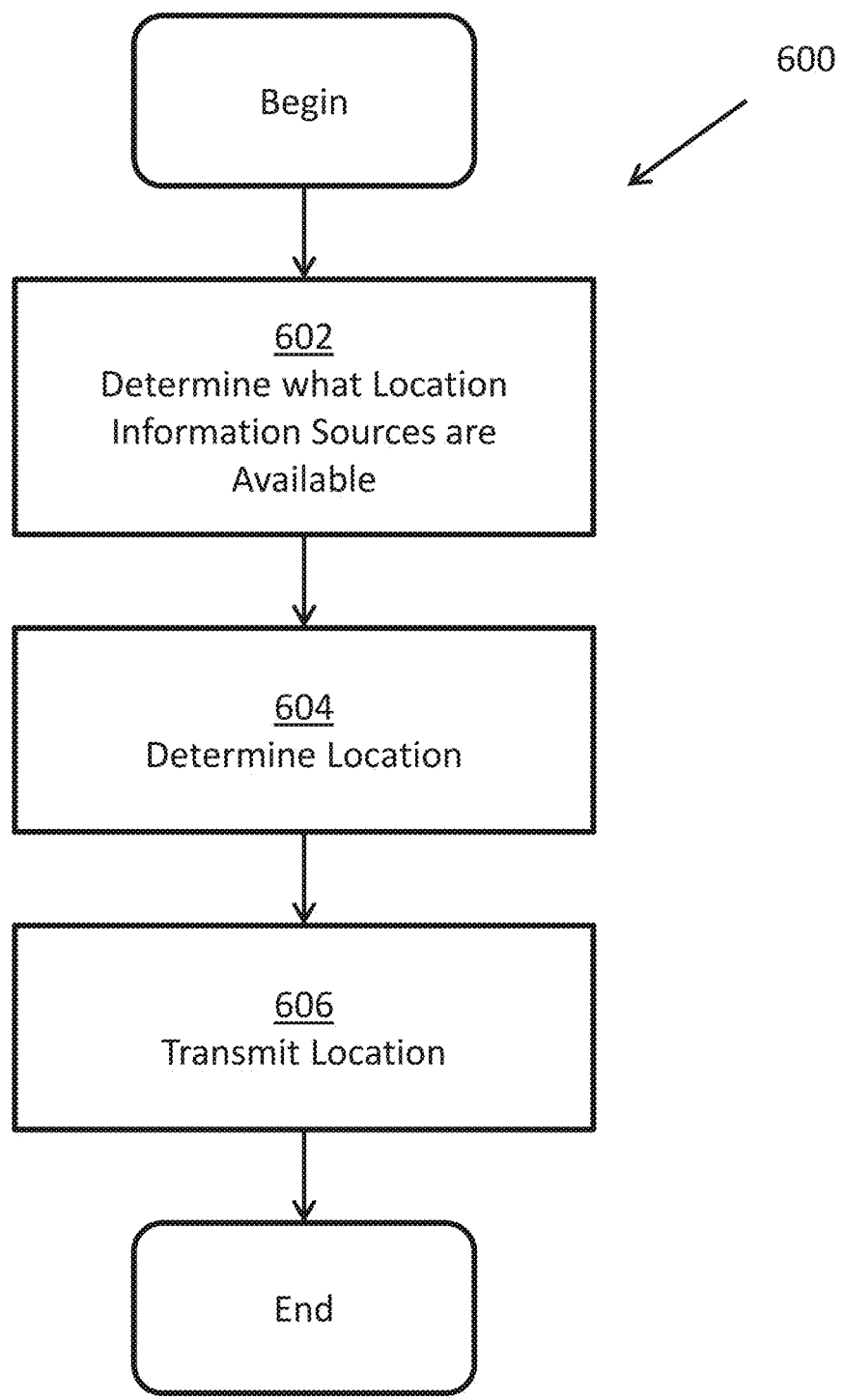
FIG. 6 is a flowchart of an example process for determining and transmitting the location of the medical device.

Various embodiments implement and enable processes through which a medical device determines and transmits its location. FIG. 6 illustrates one such process 600 that includes acts of scanning location information sources 602, determining the location of the medical device 604, and transmitting the location of the medical device 606.

In act 602, the medical device determines what location information sources are available. In some embodiments, act 602 can comprise scanning for signals corresponding to location information sources. Location information sources may include GPS sources, cellular network sources, WLAN access points, BLUETOOTH sources, RFID sources, and other medical devices. In one embodiment, the act 602 includes the act of determining a signal strength for each location information source and determining whether the signal strength is above a threshold. Where the signal strength is above the threshold, the location information source is used by the medical device as an available location information source in act 604. Otherwise, the signal strength is deemed to be too poor and the location information source is not used by the medical device in act 604. For example, the medical device may determine that the signal strength of GPS signals from satellites is too weak. In this example, GPS location information is not used in the determination of the medical device location.

Location information sources may also include hardware and/or software internal to the medical device (e.g., integrated into the same housing as the device) or local to the medical device (e.g., communicably coupled to the medical device via a short-range wired or wireless communication link). For example, the medical device may optionally include or be communicably coupled with a compass or magnetometer configured to calculate or determine a heading (e.g., a direction of travel) associated with the device. The medical device may also optionally include or be communicably coupled with one or more gyroscopes and/or other types of inertial sensors that can determine changes in a speed or velocity of the medical device. Based on data from the compass, magnetometer, gyroscope, and/or other types of inertial sensors, the medical device may continuously calculate changes in displacement of the medical device. The medical device may then estimate its current location using an inertial navigation system that uses dead reckoning. Dead reckoning can include, for example, determining the medical device's current location by adding the continuously updated displacement to a previously known location of the medical device.

In some embodiments, the medical device may also optionally include or be coupled with a pressure sensor that can measure the ambient air pressure, and detect changes in the air pressure. Based on the measured air pressure, the medical device may estimate the current altitude of the medical device. In some embodiments, this estimated altitude may be used to estimate what floor, or what range of floors, the medical device is on within a multi-story building. Optionally, the medical device may combine the estimated altitude with stored topographical data to estimate the medical device's current location.

Also in some embodiments, the medical device may include or be coupled with sensors that can determine important contextual information regarding the medical device's location. For example, the medical device may include or be coupled with ultrasonic or infrared sensors configured to locate and map the medical device's local surroundings, such as objects, furniture, walls, and hallways, and/or the like. The medical device may also include a temperature sensor configured to measure the ambient air temperature at the medical device's location. These ultrasonic, infrared, and/or temperature sensors may provide important context regarding the medical device's current location, such as whether the medical device is in an enclosed space or an open space, whether the medical device is near a wall or two walls, or within a corridor-like environment, whether the medical device is indoors or outdoors, and/or the like. Even if these information sources cannot determine an exact location of the medical device on its own, such contextual information may be helpful in determining the medical device's exact location if the medical device's approximate location is already known. For instance, if it is known that the medical device is within a large auditorium, but the device's exact location is unknown, such contextual information can help establish that the medical device is near two walls, and therefore likely to be near a corner of the auditorium. Or if it is known that the medical device is somewhere on a campus-like environment, such contextual information can help establish whether the medical device is indoors or outdoors (e.g., by determining whether the ambient temperature is at room temperature, or hotter or colder than room temperature).

In act 602, the medical device can determine whether it is equipped with the necessary hardware (e.g., inertial sensors, compass/magnetometer, pressure sensors, ultrasonic and/or infrared sensors, and temperature sensors) and/or software (e.g., dead reckoning algorithms, altitude estimation software) to estimate the medical device's location. In some embodiments, in act 602, the medical device may determine whether these information sources that are internal to and/or local to the medical device have sufficient data to estimate the medical device's current location.

In act 604, the medical device determines location information. Actions performed by the medical device controller during execution of act 604 are described further below with reference to FIG. 7.

In act 606, the medical device may transmit the location information determined in act 604. For example, the medical device may transmit the location information for the medical device to a system operated by a medical dispatcher to dispatch medical personnel. Additionally or alternatively, the medical device may transmit the location information determined in act 604 to one or more wearable devices associated with medical personnel. For example, the medical device may transmit the location information of the medical device to a pair of computer enabled glasses, watch, and/or earpiece worn by medical personnel. Example wearable devices configured to receive location information are described further below with regard to FIGS. 9-12 and the Example Wearable Devices section of this specification.

It is appreciated that process 600, which detects and transmits the location of the medical device, may demand substantial power. Accordingly, in some embodiments, process 600 is only executed when a critical patient event is detected. For example, the medical device may execute process 600 when a health disorder associated with the patient is detected (e.g., ventricular fibrillation or ventricular tachycardia) that necessitates immediate medical attention.

Figure 7:
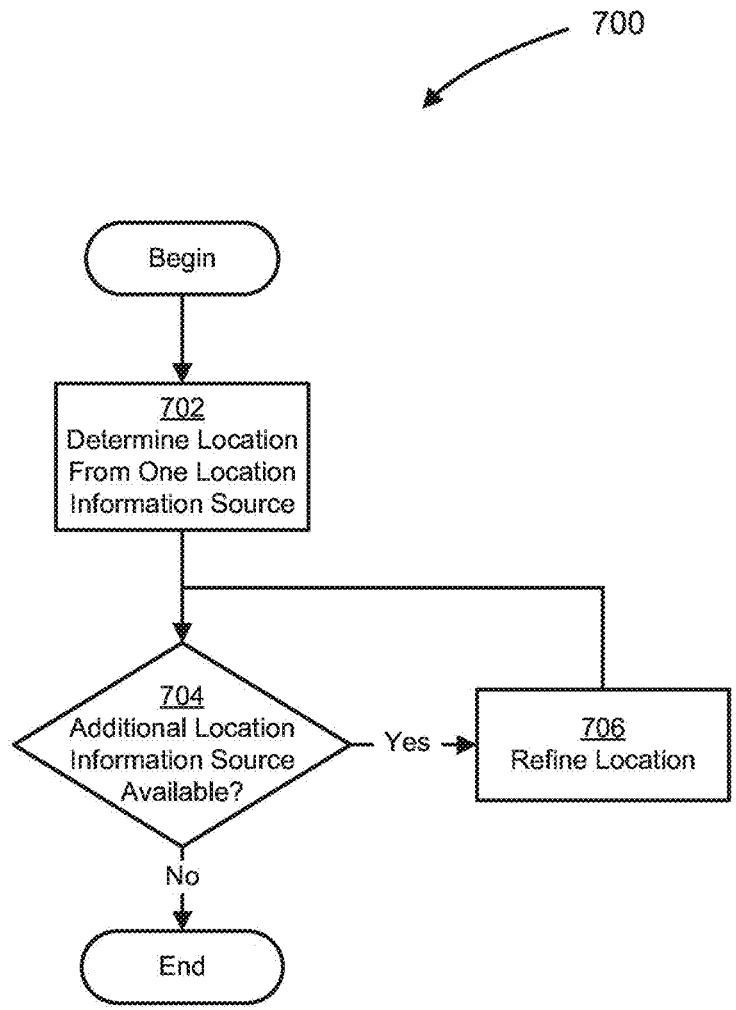
FIG. 7 is a flowchart of an example process for determining the location of a medical device.

As discussed above with regard to act 604 in FIG. 6, various embodiments implement processes for determining the location of a medical device. FIG. 7 illustrates one such process 700 that implements the act 604 and that includes acts of determining device location area from a location information source 702, determining whether additional location information sources are available 704, and refining the location 706.

In act 702, the medical device determines a location of the medical device with a given level of accuracy based upon a single location source. The single location source is selected consistent with a hierarchy of location information sources. The highest ranked available location information source in the hierarchy is selected. An example hierarchy 800 is illustrated with regard to FIG. 8 and the Example Hierarchy of Location Information Sources section of this specification.

In act 704, the medical device determines whether any additional location information sources are available. If the medical device determines that any additional location information sources are available, the medical device determines which available location information source is the next highest ranked in the hierarchy of location information sources and proceeds to act 706. Otherwise, the medical device terminates process 700.

In act 706, the medical device applies the location information gathered from the additional available location information source to improve the accuracy of the location of the medical device. After improving the accuracy of the medical device location, the medical device proceeds to act 704 to check to see if any additional location information sources are available. For example, an approximate location of the medical device may have been computed based upon GPS location information in act 702. The approximate location based upon the GPS location information can be a circle of a given radius (e.g., 50 meters). The medical device then determines that one or more WLAN access point location information sources are available in act 704. In act 706, in this embodiment, the medical device communicates with a coordinate database in a central server that contains the coordinates of the WLAN access point location information sources. The medical device determines the distance between itself and each of the one or more WLAN access points. The medical device then determines the approximate location that meets all of the constraints (e.g., circle of a given radius computed from the GPS location information, and the distances between the known WLAN access points), thus improving the level of accuracy of the approximate medical device location. Accordingly, the area within which the medical device is likely to be located has reduced.

Additional ways of improving the approximate location based upon information from the additional location information source are also possible. For example, instead of using WLAN access point location information sources, the medical device can use cellular tower location information sources, Bluetooth information sources, other medical device information sources, and/or RFID information sources in the same fashion described above. In some embodiments, the approximate location of the medical device determined in act 702 can include only information locating the device in two dimensions, e.g., latitude and longitude. However, if the medical device is in a multi-story building, altitude information from a pressure sensor internal to and/or coupled with the medical device can be used to estimate what floor, or what range of floors, the medical device is on. Or, the approximate location of the medical device determined in act 702 may be precise enough to put the medical device within a large building, or campus-like environment, but may not be precise enough to locate the medical device within a specific part of the building, or a specific part of the campus. Information from the additional location information source can be used to determine whether the medical device is located in an indoor location, an outdoor location, an enclosed space, an open space, or a space with one, two, or three nearby walls, for example. This information can then be used to refine the approximate location in act 702 by narrowing down the location(s) at which the medical device could be located. In these ways, the area within which the medical device is likely to be located can be reduced.

It is appreciated that a subset of the acts or all of the acts of process 700 for determining location information may be performed by the central server. For example, medical device may transmit the available location information sources to the central server. The central server then performs process 700 and determines the location of the medical device. As another example, the medical device may transmit contextual information regarding its surrounding environment, such as the local air temperature, air pressure, and/or information regarding nearby walls/objects to the central server, which may be used by the central server to refine the approximate location of the medical device. The location of the medical device may be transmitted to the medical device, transmitted directly to a remote system operated by medical personnel as shown in act 604 with reference to FIG. 6, or both.

In one embodiment, the medical device has a configurable accuracy parameter that specifies a threshold level of accuracy after which the medical device does not search for further location information sources. In this embodiment, within the act 704, the medical device evaluates the location information to determine whether the accuracy parameter has been met. If so, the medical device terminates the refinement process 700. Otherwise, the medical device continues execution of the act 704 (i.e., determines whether additional location information sources are available). For instance, in an example where the accuracy parameter specifies an accuracy of five meters and the medical device determines location information accurate to within five meters from information gathered from the first two levels of the hierarchy (e.g., GPS and WLAN access point location information sources), the medical device terminates the refinement process 700 without searching for additional information sources in the hierarchy.

Each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a medical device configured according to the examples disclosed herein.

Example Hierarchy of Location Information Sources

Various embodiments implement and enable various location information hierarchies through which a medical device determines its location. FIG. 8 illustrates an example hierarchy of location information sources 800 employed by the medical device controller including a first level 802 with GPS information sources, a second level 804 with cellular tower information sources, a third level 806 with WLAN access point information sources, a fourth level 808 with other medical device information sources, a fifth level 810 with BLUETOOTH information sources, a sixth level 812 with RFID information sources, and a seventh level 814 with internal or local information sources.

The hierarchy of location information sources 800 illustrates one hierarchy with which the medical device may determine its location. The first level 802 (e.g., GPS location information sources) is the highest ranked location information source. Embodiments configured to reference the hierarchy 800 determine location information for a medical device based on GPS information sources in act 702 of FIG. 7 if GPS sources are available. Otherwise, these embodiments proceed to the lower levels (e.g., the second level 804 through the sixth level 812) of the hierarchy to determine the location information. For example, the medical device may proceed to find location information sources consistent with the second level of the hierarchy (e.g., cellular tower point location information sources) if no GPS location information sources are available. Once location information for the medical device has been computed with the highest ranked available location information source, any information sources available with a lower ranking in the hierarchy than the information source used in act 702 are used to further improve the accuracy of the medical device location. It is appreciated that the medical device may stop moving down the hierarchy to improve the accuracy of the location once it has reached a threshold level of accuracy.

Example Wearable Devices

As discussed above, various embodiments of a medical device disclosed herein transmit information descriptive of a determined location to an external device. The external device may include, for example, a wearable device worn by medical personnel to identify the location of the patient receiving therapy from a medical device in the field. The term wearable device refers to a computer enabled device with a connection mechanism to removably secure the device to at least one part of a subject. Wearable devices include, for example, watches, glasses, or earpieces with a processing unit.

Figure 9:
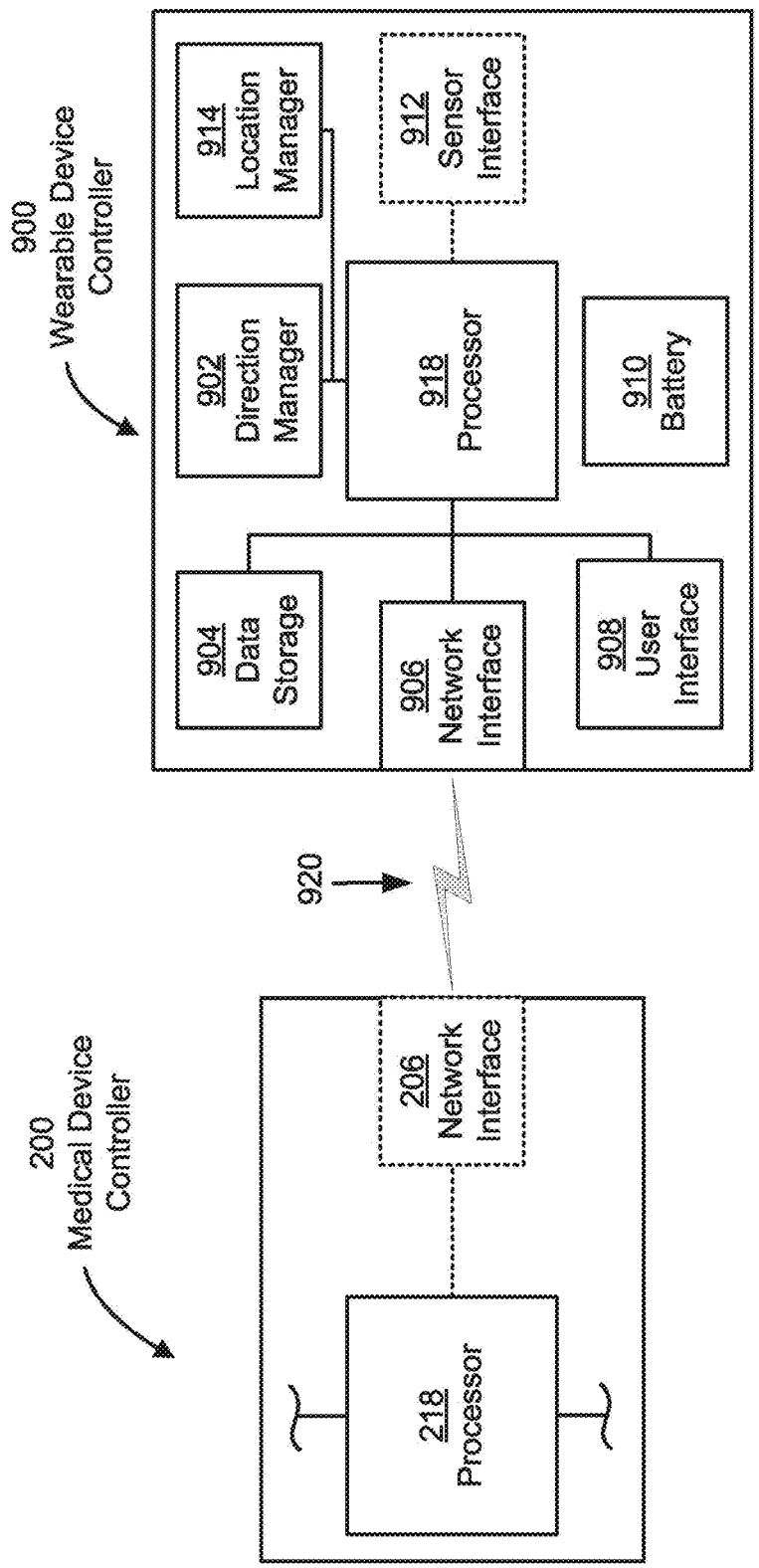
FIG. 9 is an illustration of an example wearable device controller in communication with an example medical device controller.

FIG. 9 illustrates an example wearable device controller 900 within a wearable device in communication with a medical device controller 200. The wearable device controller 900 is constructed to receive location information from the medical device controller 200 by, for example, wireless communication link 920 and guide a subject wearing the wearable device to the received location. The wearable device controller 900 includes a battery 910 and a processor 918 coupled to a direction manager 902, a location manager 914, a data storage 904, a user interface 908, network interface 906, and an optional sensor interface 912.

The wearable device controller 900 receives the location of the medical device from the medical device controller 200 via network interface 906. The network interface 906, as described in more detail further below, facilitates the creation of the wireless communication link 920 between the wearable device controller 900 and the medical device controller 200. It is appreciated that the wireless communication link 920 may be a direct wireless communication link or an indirect wireless communication link. For example, the medical device controller 200 may transmit the location of the medical device to a local cellular tower and the cellular network may transmit the location of the medical device to the wearable device via, for example, a cellular tower near the wearable device. In addition, information other than location information may be transmitted via wireless communication link 920. For example, information regarding the medical condition of the patient may be transmitted from the medical device controller 200 to the wearable device controller 900. Information regarding the local environment of the medical device may also be transmitted from the medical device controller 200 to the wearable device controller 900. Such information may include, for example, local ambient air pressure, local air temperature, presence of and/or distance to surrounding walls, objects, furniture, and/or the like. Such contextual information may be used by the wearable device controller 900 to refine the location of the medical device, as described above.

The processor 918 performs a series of instructions that result in manipulated data which are stored in and retrieved from the data storage 904. According to a variety of embodiments, the processor 918 is a commercially available processor such as a processor manufactured by Texas Instruments, Intel, AMD, Sun, IBM, Motorola, Freescale, and ARM Holdings. However, the processor 918 may be any type of processor, multiprocessor or controller, whether commercially available or specially manufactured. In addition, in several embodiments the processor 918 is configured to execute a conventional real-time operating system (RTOS), such as RTLinux. In these embodiments, the RTOS may provide platform services to application software, such as some embodiments of the location manager 914 which is discussed further below. These platform services may include inter-process and network communication, file system management and standard database manipulation. One or more of many operating systems may be used, and embodiments are not limited to any particular operating system or operating system characteristic. For instance, in some embodiments, the processor 918 may be configured to execute a non-real time operating system, such as BSD or GNU/Linux.

The location manager 914 is configured to determine the location of the wearable device. In some embodiments, the location manager 914 employs processes similar to the processes previously described with reference to FIGS. 6-8 discussed above. In these embodiments, it is appreciated that the location manager 914 may omit step 606 of transmitting the location of the wearable device in FIG. 6. It is appreciated that the location manager 914 may employ other methods to determine the location of the wearable device. For example, the location manager 914 may receive GPS signals from satellites via network interface 906 and determine the location of the wearable device with a given level of accuracy based on the received GPS signals.

It is also to be appreciated that the wearable device may be communicably coupled, via a wired or wireless connection, to other devices in the local vicinity of the subject wearing the wearable device. Such other devices may comprise additional sensors, hardware or software that may provide information to location manager 914 to help location manager 914 determine the wearable device's location. For instance, the wearable device may be communicably coupled to one or more user devices, such as a smartphone or another wearable device. These one or more user devices may be configured to determine its location using GPS, cellular network towers, WLAN, BLUETOOTH, RFID, and other information sources. The one or more user devices may also comprise pressure sensors, temperature sensors, and ultrasonic or infrared sensors which may be used to determine contextual information regarding the user devices' surroundings, as described above. The one or more user devices can then pass on this information to location manager 914 to help location manager 914 determine the location of the wearable device.

The direction manager 902 is configured to provide directions to the subject wearing the associated wearable device. Direction manager 902 may receive the location of the medical device via, for example, network interface 906. The direction manager 902 issues directions via, for example, the user interface 908. The particular method employed to guide the subject may be tailored to the particular embodiment of the wearable device associated with the wearable device controller 900. Examples of various wearable devices are described further below with reference to FIGS. 10, 11, and 12.

In some embodiments, the direction manager 902 receives, via the one or more antennas coupled to the network interface 906, information descriptive of a location of the medical device. The direction manager 902 may be configured to determine a path between the location of the wearable device, as identified by the location manager 914, and the location of the medical device. The direction manager 902 may provide, via the user interface 908, directions to the subject regarding the determined path. It is appreciated that the direction manager 902 may transmit messages to the medical device controller 200 to facilitate the subject locating the medical device. For example, the direction manager 902 may transmit, via the network interface 906, a notification to the medical device controller 200 to make an audible alert responsive to the subject being within a threshold distance of the medical device.

The direction manager 902, in some embodiments, is configured to provide medical information regarding the patient medical condition information to the subject. For example, the medical device may transmit information descriptive of a heart rate of the patient with the location of the medical device and the wearable device may display the heart rate of the patient and/or direction to guide the medical personnel to the medical device. Status identifiers associated with the overall medical condition of the subject may be displayed to the subject. For example, green, yellow, and red status identifiers may be displayed for patients in good, fair, and poor medical condition, respectively. It is appreciated that the wearable device controller 900 may trigger the production of medical information from the medical device controller 200. For example, the wearable device controller 900 may receive, via user interface 908, a command from the subject to provide patient medical condition information and send a request to the wearable device controller 200 requesting the patient medical information.

The location manager 914 and/or the direction manager 902 may be implemented using hardware or a combination of hardware and software. For instance, in one embodiment, the location manager 914 and/or the direction manager 902 is implemented as a software component that is stored within the data storage 904 and executed by the processor 918. In this embodiment, the instructions included in the location manager 914 program the processor 918 to determine the location of the medical device and/or the instructions included in the guide manager 902 program the processor 918 to guide a subject to the location of a medical device. In other embodiments, the location manager 914 and/or the direction manager 902 may be an application-specific integrated circuit (ASIC) that is coupled to the processor 918. Thus, embodiments of the location manager 914 and/or the direction manager 902 are not limited to a particular hardware or software implementation.

In some embodiments, the components disclosed herein, such as the location manager 914 and the direction manager 902, may read parameters that affect the functions performed by the components. These parameters may be physically stored in any form of suitable memory including volatile memory, such as RAM, or nonvolatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some embodiments provide for both system and user interfaces, as may be implemented using the user interface 908, that allow external entities to modify the parameters and thereby configure the behavior of the components.

The data storage 904 includes a computer readable and writeable nonvolatile data storage medium configured to store non-transitory instructions and data. In some embodiments, the data storage 904 is similar to the data storage 204 previously described above with reference to FIG. 2. It is appreciated that the data storage 904 may store specialized data for the location manager 914 and/or the direction manager 902. For example, the data storage 904 may store location information including information that identifies the plurality of location information sources.

As shown in FIG. 9, the wearable device controller 900 includes several system interface components including network interface 906, user interface 908, and optional sensor interface 912. Each of these system interface components is configured to exchange, i.e. send or receive, data with one or more specialized devices that may be located within the housing of the wearable device controller 900 or elsewhere. The components used by the interfaces 906, 908, and 912 may include hardware components, software components or a combination of both. Within each interface, these components physically and logically couple the wearable device controller 900 to the specialized devices. This physical and logical coupling enables the wearable device controller 900 to communicate with and, in some instances, power or control the operation of the specialized devices. These specialized devices may include physiological sensors and computer networking devices.

As discussed above, the system interface components 906, 908, and 912 shown in the embodiment of FIG. 9 support different types of specialized devices. For instance, the components of the sensor interface 912 couple the processor 918 to one or more physiological sensors such as a body temperature sensors, respiration monitors, and electrocardiogram (ECG) sensing electrodes, one or more environmental sensors such as atmospheric thermometers, airflow sensors, video sensors, audio sensors, accelerometers, GPS locators, and hygrometers. In these embodiments, the sensors may include sensors with a relatively low sampling rate, such as wireless sensors.

The user interface 908 shown in FIG. 9 includes a combination of hardware and software components that allow the wearable device controller 900 to communicate with an external entity, such as a patient or other user. These components may be configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens, speakers, and electromechanical vibrators. In some embodiments, the electrodes include an illuminating element, such as an LED. In other embodiments, the printing devices include printers capable of rendering visual or tactile (Braille) output.

According to various embodiments, the network interface 906 enables communication between the wearable device controller 900 and a variety of electronic devices including, for example, other wearable devices or medical devices. In other embodiments, the network interface 906 includes both a physical interface configured for wireless communication and a physical interface configured for wired communication. To ensure data transfer is secure, in some embodiments, the wearable device controller 900 can transmit data via the network interface 906 using a variety of security measures including, for example, TLS, SSL or VPN.

In one embodiment, the network interface 906 is also capable of transmitting and/or receiving information to assist in wearable device location determination. This may be accomplished through one or more antennas integrated with or coupled to the network interface 906, and consequently coupled to the processor 918. For example, the one or more antennas may receive GPS signals from satellites. The GPS signals may be used to determine the location of the wearable device with a given level of accuracy and/or used to determine the current time. In other embodiments, an RFID reader is integrated or coupled to the network interface 906, and coupled to the processor 918. The RFID reader may be used at least in part to determine the location of the wearable device. For example, the wearable device may have access to a coordinate database that includes RFID tag locations and determine its location at least in part by detecting an RFID tag with a known location within a given range of the wearable device. The database may be stored locally in the memory of the wearable device controller 900 or in a central server. It is appreciated that the systems described above with regard to connecting to various networks (e.g., wireless Ethernet or BLUETOOTH) may be used as probes to find known reference points within a given range. For example, the wearable device controller 900 may detect a WLAN access point or a BLUETOOTH source with known positions stored in a database accessible by the wearable device controller 900. The wearable device controller 900 may be able to determine its location at least in part by determining the distance between the wearable device controller and the known location of the WLAN access point or BLUETOOTH source. This may be accomplished at least in part by analyzing the signal strength of the WLAN access point and BLUETOOTH source.

It is appreciated that the wearable device location computation may be performed in a collaborative fashion with the central server to minimize the computations performed by the wearable device controller. For example, the wearable device may transmit the detected sources and their respective signal strengths. The central server may then compute the location of the wearable device by analyzing the signal strengths and coordinates associated with the sources. The computed wearable device location may then transmit to the wearable device or a remote system (e.g., a remote system operated by medical personnel).

The wearable device controller 900 has a variety of potential applications and is well suited to devices that guide medical personnel to a deployed medical device. Examples of devices to which the wearable device controller 900 is well suited include computer enabled watches, glasses, and earpieces as described below with references to FIGS. 10-12.

Figure 10:
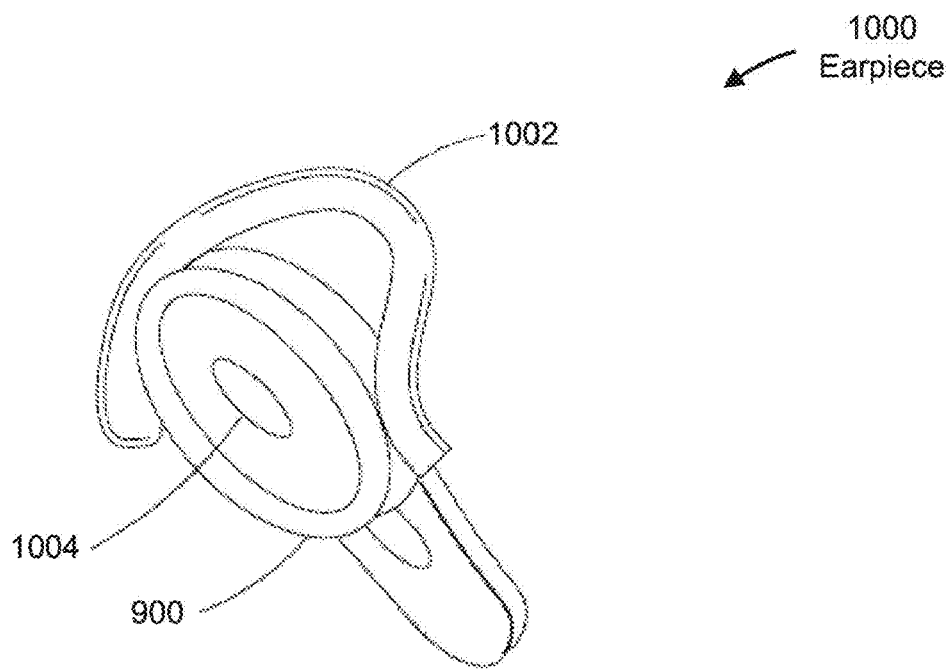
FIG. 10 is an illustration of an example wearable device.

FIG. 10 illustrates an example wearable device in the form of an earpiece 1000. It is appreciated that the term earpiece refers to a wearable device that can be removably secured to the ear of a subject. As shown, the earpiece 1000 includes a clip 1002 constructed to be disposed about the subject's ear, wearable device controller 900, and an optional button 1004. Although not visible, in FIG. 10, the earpiece wearable device 1000 includes an audio output device, such as a speaker, constructed to be disposed proximate the patient's ear canal for audibly communicating messages. The audio output device may be coupled to the user interface component 908 of the wearable device controller 900 and communicate directions to the subject.

The earpiece 1000, in some embodiments, includes a microphone coupled to, for example, the user interface component 908. In this embodiment, the microphone may receive voice commands from the subject and the wearable device controller 900 may perform an action based on the voice command. For example, the subject may issue a voice command to "Get Patient Condition Information" and the wearable device controller 900 may gather the information regarding the medical condition of the patient from the medical device and communicate the information to the subject. In other embodiments, the microphone may be employed as part of a hearing aid. For example, the microphone may detect ambient sound including a person's voice in a noisy environment and the wearable device controller 900 may process the received ambient sound to attenuate background noise, amplify the person's voice, and communicate the amplified person's voice to the subject.

The earpiece 1000, in some embodiments, includes one or more physiological sensors to monitor various physiological parameters of the subject. For example, the one or more physiological sensors may include a pulse oxygen sensor that monitors the subject's pulse oxygen level as the human ear is considered to be a relatively good location at which to measure the pulse oxygen level. It is appreciated physiological parameters of the subject other than pulse oxygen level may be monitored by the earpiece 1000.

Figure 11:
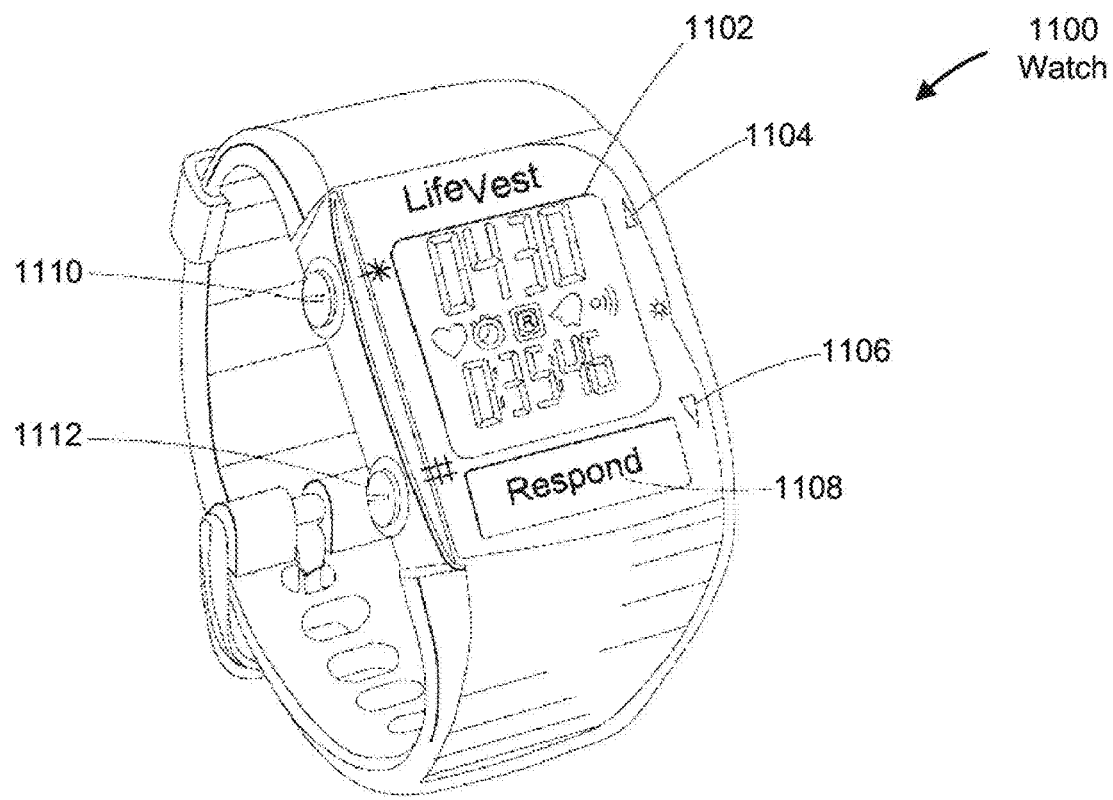
FIG. 11 is an illustration of another example wearable device.

FIG. 11 illustrates an example wearable device in accordance with aspects of the present invention in the form of a watch 1100. It is appreciated that the term watch refers to a wearable device that can be removably secured to the wrist of a subject and may or may not display and/or determine the current time. The watch 1100 includes a strap to removably secure the watch to a wrist of a subject.

As shown in FIG. 11, the watch 1110 includes a display 1102, buttons 1110 and 1112, scrolling buttons 1104 and 1106, and response button 1108. It is appreciated that the watch 1100 includes a wearable device controller 900 within, for example, a housing.

In some embodiments, the display 1102 is coupled to the user interface component 908 and presents content to the subject including, for example, a current date, a current time, directions to a medical device, location of the medical device, and patient medical condition information. When displaying the location of the medical device, and/or directions to the medical device, display 1102 can be configured to display an indication of an accuracy or confidence-level associated with the location of the medical device. For instance, display 1102 can display circles on a map corresponding to an expected location of the medical device, wherein the circles are of different sizes depending on an accuracy associated with the expected location. In some embodiments, the diameter of the circles can correspond to an expected accuracy of the medical device's location. Such circles can also be colored different colors depending on location accuracy—for example, green can be used for circles that are 6 feet in diameter or smaller, yellow can be used for circles that are 100 feet in diameter or smaller, and red can be used for circles that are larger than 100 feet in diameter. It is to be appreciated that the aforementioned numerical breakpoints are exemplary only, and many different numerical ranges, as well as numbers and types of colors, can be employed. Other ways of expressing an indicator associated with an accuracy or confidence-level in the medical device's location, such as a text indicator, an icon, or use of color in different ways, are also possible.

As described above, the wearable device controller 900 may receive, or be instructed to gather, patient medical condition information. The wearable device controller 900 may present information representative of the patient medical condition via the display 1102 to the subject. For example, the wearable device controller 900 may present a heart icon via display 1102 to indicate that the patient is suffering from an arrhythmia. In addition, the user interface component 908 may vibrate the watch 1100 via an electromechanical vibrator responsive to receiving the patient medical condition information to alert the subject to the presence of new patient information.

The scrolling buttons 1104 and 1106, in some embodiments, are coupled to the user interface component 908. The user interface component 908 may scroll the content displayed on display 1102 based on the input received from the scrolling buttons 1104 and 1106.

The watch 1100, in some embodiments, includes physiological sensors coupled to the sensor interface 912. The physiological sensors may include, for example, sensors disposed on the back side of the watch 1100 to detect the pulse rate, temperature, or blood oxygen level of the subject. Such information may be displayed via display 1102 to the subject.

In one embodiment, the watch 1100 includes an audio output device coupled to the user interface 908 to issue alarms or audible messages to the subject. For example, the wearable device controller 900 may issue audible directions to the subject via the audio output device.

Figure 12:
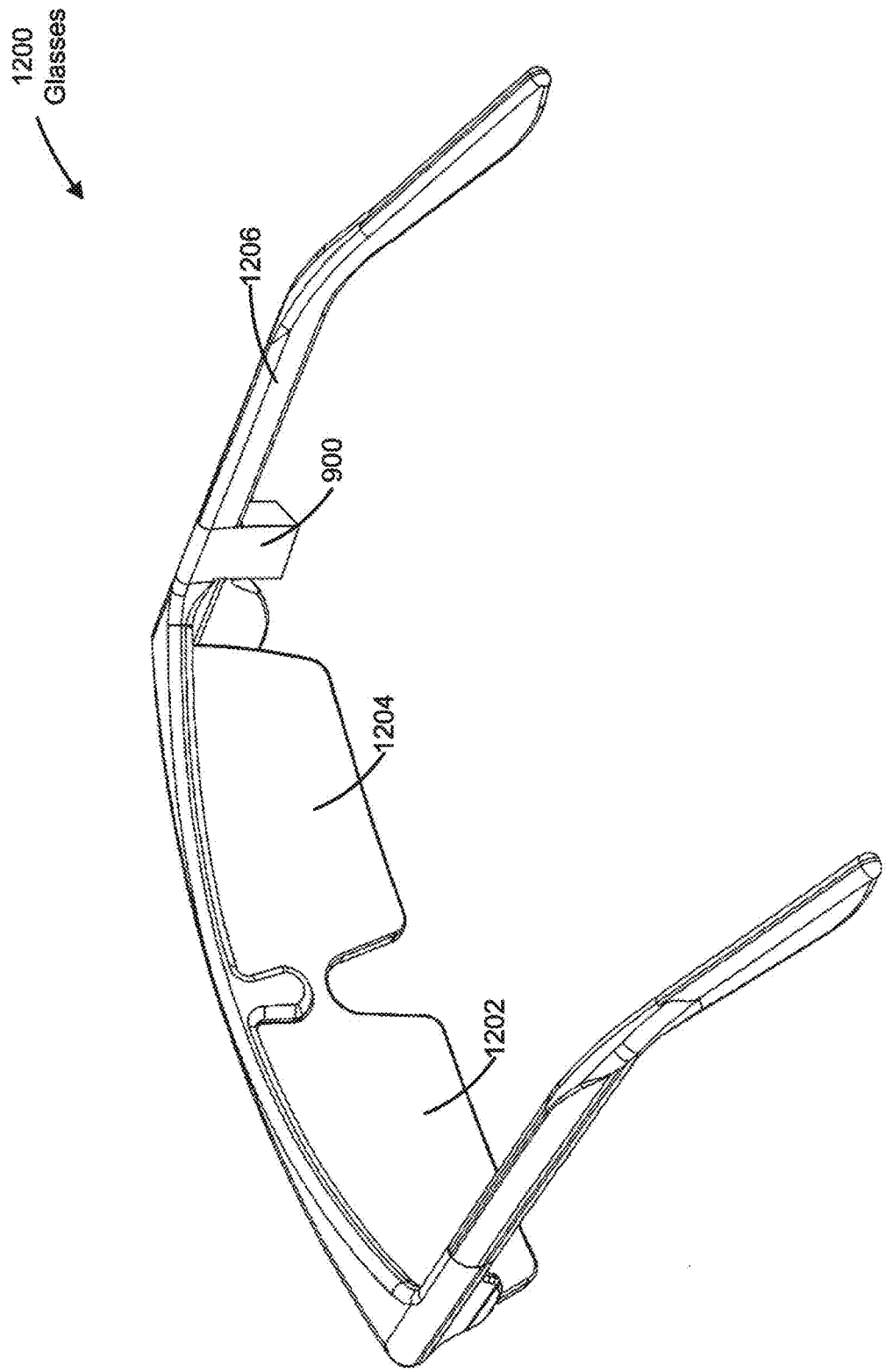
FIG. 12 is an illustration of another example wearable device.

FIG. 12 illustrates an example pair of glasses 1200 in accordance with some embodiments of the present invention. It is appreciated that the term glasses refers to a wearable device removably secured to the head of a subject. As shown, the glasses 1200 include a wearable device controller 900, a left lens 1202, a right lens 1204, and temples 1206. The temples 1206 are constructed to removably secure the glasses 1200 to the head of a subject.

The glasses 1200, in some embodiments, include a display to present content (e.g., directions) to the user. The display may include a display lens. For example, at least one of the left lens 1202 and the right lens 1204 may be coupled to the wearable device controller 900 and configured to display content to the subject. It is appreciated that other displays may be employed in the glasses 1200. For example, the glasses 1200 may include a projector coupled to the user interface component 908 that is configured to project light into a prism disposed in front of at least one of the lenses to display content to the subject. The wearable device controller 900 may present directions to the subject by displaying directional arrows pointing towards the location of the medical device to the subject. The wearable device controller 900 may also display the location of the medical device on a map, along with an indicator of an accuracy or confidence-level associated with the location, as described above in relation to FIG. 11.

The wearable devices 1000, 1100, and 1200 described in FIGS. 10-12 above may be used in combination and communicate with each other. For example, wearable devices 1000, 1100, and 1200 may be worn by the same subject simultaneously and communicate via the network interface 906. The direction manager 902 in each of the wearable devices may coordinate to provide guidance to the subject. For example, the glasses 1200 may display a directional arrow to the subject indicating a right turn while the earpiece 1000 simultaneously provides an audible instruction to the subject to "Turn Right."

Example Wearable Device Processes

Figure 13:
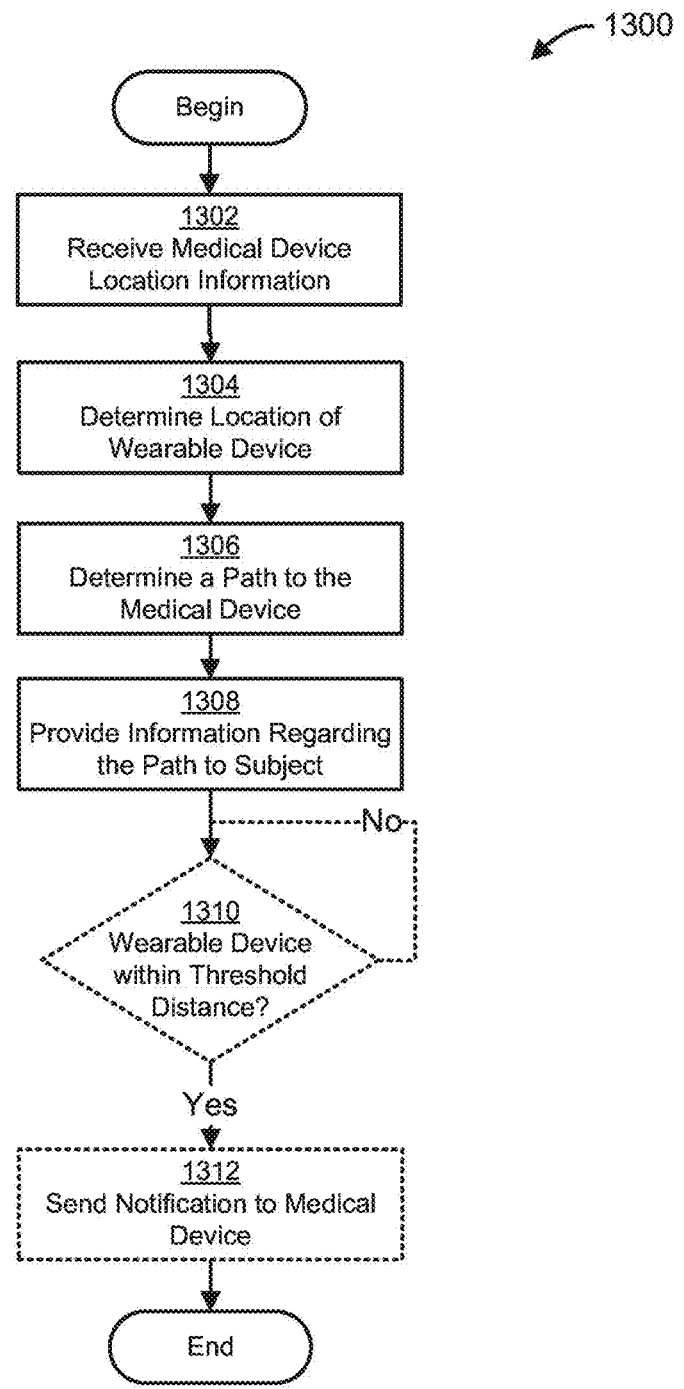
FIG. 13 is an illustration of an example wearable device process.

Various embodiments implement and enable processes through which a wearable device determines its location relative to a medical device and provides instructions to the subject to guide the subject towards the medical device. FIG. 13 illustrates one such process 1300 that includes the acts of receiving medical device location information 1302, determining a location of the wearable device 1304, determining a path to a medical device 1306, and providing information regarding the path to the subject 1308. Process 1300 may optionally further includes acts of determining whether the wearable device is within a threshold distance of the medical device 1310 and sending a notification to the medical device 1312.

In act 1302, the wearable device receives location information descriptive of the location of the medical device. The wearable device may receive this information via, for example, one or more antennas coupled to the network interface component 906 in the wearable device controller 900.

In act 1304, the wearable device determines its location. The wearable device may determine its locations consistent with process 700 previously described. It is appreciated that other methods may be employed to determine the location of the wearable device. For example, the wearable device may employ only GPS information to determine its location.

In act 1306, the wearable device determines a path to the medical device. The wearable device may determine the path to the medical device by analyzing one or more maps (e.g., roadmaps, building maps, and/or the like) and selecting a path with the shortest distance between the location of the medical device and the location of the wearable device. The various maps employed by the wearable device may be stored locally in, for example, data storage 904 of the wearable device controller 900 and/or received from another electronic device via network interface 906. It is appreciated that the wearable device may also select paths based on an estimated travel time. For example, the wearable device controller may determine an estimated travel time associated with each path and select the path with the shortest travel time, which may not be the shortest distance.

In act 1308, the wearable device provides information regarding the path to the subject. For example, the wearable device may provide audible instructions regarding the path and/or display directions to the subject. It is appreciated that the particular method employed to communicate the messages to the subject vary based on the particular type of wearable device employed. For example, audible instructions may be employed in earpiece wearable devices while visual instructions and/or audible instructions may be employed in watch wearable devices.

In optional act 1310, the wearable device determines whether the wearable device is within a threshold distance of the medical device. The wearable device may determine that the wearable device is within a threshold distance of the medical device by comparing the location of the medical device with the location of the wearable device. If the wearable device determines that it is within the threshold distance of the medical device, the wearable device proceeds to optional act 1312 and sends a notification to the medical device. Otherwise, the wearable device continues to monitor the distance between the wearable device and the medical device in act 1310. The notification sent to the medical device in act 1312 may include, for example, an instruction for the medical device to issue an alarm or other sound to communicate its location to the subject.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

The invention claimed is:

1. A wearable device for directing emergency personnel to a medical device separate from the wearable device, the wearable device comprising:

memory storing computer-executable instructions;
one or more antennas;
one or more processors coupled with the memory and the one or more antennas,
the one or more processors being configured to execute the computer-executable instructions to:
receive, via the one or more antennas, location information from at least one location information source external to the wearable device;
estimate a location of the wearable device based on the received location information;
transmit, via the one or more antennas, the estimated location of the wearable device to at least one server;
receive, via the one or more antennas, information descriptive of a location of at least one medical device separate from the wearable device;
determine a path between the location of the wearable device and the location of the at least one medical device; and
provide one or more of audible and visual information descriptive of the path.

2. The wearable device of claim 1, wherein the at least one location information source comprises at least one of a GPS source, cellular network source, satellite, WLAN access point, a Bluetooth source, and an RFID tag.

3. The wearable device of claim 1, wherein the location information comprises an identifier for the at least one location information source.

4. The wearable device of claim 3, wherein the one or more processors are further configured to execute the computer-executable instructions to transmit a strength of a signal received from the at least one location information source to the at least one server.

5. The wearable device of claim 1, wherein the wearable device comprises at least one of an earpiece, a pair of glasses, and a watch.

6. The wearable device of claim 1, wherein the wearable device further comprises a display, and the one or more processors are configured to provide the information descriptive of the path by displaying directions regarding the path via the display.

7. The wearable device of claim 1, wherein the one or more processors are configured to transmit, via the one or more antennas, a notification to the medical device to issue an audible sound so as to assist the emergency personnel to locate the medical device when the wearable device is within a threshold distance of the medical device.

8. A system for directing emergency personnel to a medical device, the system comprising:

one or more servers having a location database that stores geographic location for a plurality of medical devices;
a wearable device separate from the plurality of medical devices, the wearable device comprising one or more antennas and one or more processors configured to:
receive, via the one or more antennas, location information from at least one location information source external to the wearable device;
estimate a location of the wearable device based on the received location information;
transmit, via the one or more antennas, the estimated location of the wearable device to the one or more servers;
receive, via the one or more antennas, information descriptive of a location of at least one of the plurality of medical devices;

determine a path between the location of the wearable device and the location of the at least one medical device; and provide one or more of audible and visual information descriptive of the path.

9. The system of claim 8, wherein:

the location information received from the at least one location information source external to the wearable device comprises an identifier for the at least one location information source; and the location of the wearable device received from the at least one server is derived at least in part from the geographic location stored in the location database for the location information source corresponding to the identifier.

10. The system of claim 9, wherein:

the one or more processors of the wearable device are further configured to transmit to the one or more servers a strength of a signal received from the at least one location information source; and the location of the wearable device received from the at least one server is derived at least in part based on the strength of the received signal.

11. The system of claim 8, wherein the at least one location information source comprises at least one of a GPS source, cellular network source, satellite, WLAN access point, a Bluetooth source, and an RFID tag.

12. The system of claim 8, wherein the wearable device comprises at least one of an earpiece, a pair of glasses, and a watch.

13. The system of claim 8, wherein the wearable device further comprises a display, and the one or more processors are configured to provide the information descriptive of the path by displaying directions regarding the path via the display.

14. A method for directing emergency personnel to a medical device, the method comprising:

receiving, at a wearable device, a signal communicating location information from at least one location information source of a plurality of location information sources;

estimating a location of the wearable device based on the received location information;

transmitting the estimated location from the wearable device to at least one server;

receiving, at the wearable device, information descriptive of a location of the medical device, wherein the medical device is separate from the wearable device;

determine a path between the estimated location of the wearable device and the location of the medical device; and provide one or more of audible and visual information descriptive of the path.

15. The method of claim 14, wherein the location information received by the wearable device from the at least one location information source comprises an identifier for the location information source.

16. The method of claim 15, wherein the server estimates the location of the wearable device at least in part by retrieving a geographic location for the location information source corresponding to the identifier for the location information source.

17. The method of claim 15, the method further comprising:

measuring, at the wearable device, a signal strength of the signal received from the at least one location information source; and transmitting the measured signal strength from the wearable device to the at least one server; and wherein the location of the wearable device is estimated by the at least one server based at least in part on the measured signal strength.

18. The method of claim 14, wherein the path between the estimated location of the wearable device and the location of the medical device is determined by the wearable device.

19. The method of claim 14, wherein the plurality of location information sources comprise at least one of a WLAN access point, a Bluetooth source, and a RFID tag.

20. The method of claim 14, wherein providing information descriptive of the path comprises displaying the information descriptive of the path via a display coupled to the wearable device.

* * * * *